United States Patent
Akiyama et al.

(10) Patent No.: US 11,793,477 B2
(45) Date of Patent: Oct. 24, 2023

(54) MEDICAL INFORMATION PROCESSING APPARATUS, X-RAY DIAGNOSTIC APPARATUS, AND MEDICAL INFORMATION PROCESSING PROGRAM

(71) Applicant: CANON MEDICAL SYSTEMS CORPORATION, Otawara (JP)

(72) Inventors: Masaki Akiyama, Nasushiobara (JP); Satoshi Yamashita, Utsunomiya (JP); Kazuo Imagawa, Nasushiobara (JP); Masashi Hirasawa, Otawara (JP); Tomukazu Ono, Otawara (JP); Mitsunobu Sugeno, Utsunomiya (JP); Hisato Takemoto, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 126 days.

(21) Appl. No.: 17/388,541

(22) Filed: Jul. 29, 2021

(65) Prior Publication Data
US 2022/0031271 A1    Feb. 3, 2022

(30) Foreign Application Priority Data
Jul. 29, 2020    (JP) ................. 2020-128499

(51) Int. Cl.
*A61B 6/00* (2006.01)

(52) U.S. Cl.
CPC .............. *A61B 6/486* (2013.01); *A61B 6/463* (2013.01); *A61B 6/5294* (2013.01)

(58) Field of Classification Search
CPC ......... A61B 6/00; A61B 6/486; A61B 6/5294; A61B 6/463; A61B 6/4441; A61B 6/464; A61B 6/465; A61B 6/52; A61B 8/463; A61B 8/464; A61B 8/465
See application file for complete search history.

(56) References Cited

U.S. PATENT DOCUMENTS

| | | | |
|---|---|---|---|
| 10,561,381 B2 * | 2/2020 | Wakai ................... | A61B 6/5247 |
| 2008/0009715 A1 * | 1/2008 | Kukuk ................... | A61B 6/504 |
| | | | 600/425 |
| 2008/0270080 A1 * | 10/2008 | Zong ..................... | G16H 40/63 |
| | | | 702/188 |

(Continued)

FOREIGN PATENT DOCUMENTS

| | | |
|---|---|---|
| JP | 2008-220839 A | 9/2008 |
| JP | 2017-120562 A | 7/2017 |

(Continued)

*Primary Examiner* — Jurie Yun
(74) *Attorney, Agent, or Firm* — Oblon, McClelland, Maier & Neustadt, L.L.P.

(57) ABSTRACT

A medical information processing apparatus of an embodiment includes an image acquiring unit, an event acquiring unit, a managing unit, and an output unit. The image acquiring unit sequentially acquires medical images during a treatment procedure for a subject. The event acquiring unit sequentially acquires events in the treatment procedure on the basis of the medical images during the treatment procedure. The managing unit manages the medical images and the events, in association with temporal information on the treatment procedure. The output unit outputs the medical images such that relations between the medical images and the events are able to be known.

20 Claims, 13 Drawing Sheets

(56) References Cited

U.S. PATENT DOCUMENTS

| | | | |
|---|---|---|---|
| 2019/0239859 A1 | 8/2019 | Takahashi et al. | |
| 2019/0371455 A1 | 12/2019 | Nishikado et al. | |
| 2020/0348426 A1 | 11/2020 | Kimura | |

FOREIGN PATENT DOCUMENTS

| | | |
|---|---|---|
| JP | 2019-117663 A | 7/2019 |
| JP | 2019-122562 A | 7/2019 |
| JP | 2019-130224 A | 8/2019 |

* cited by examiner

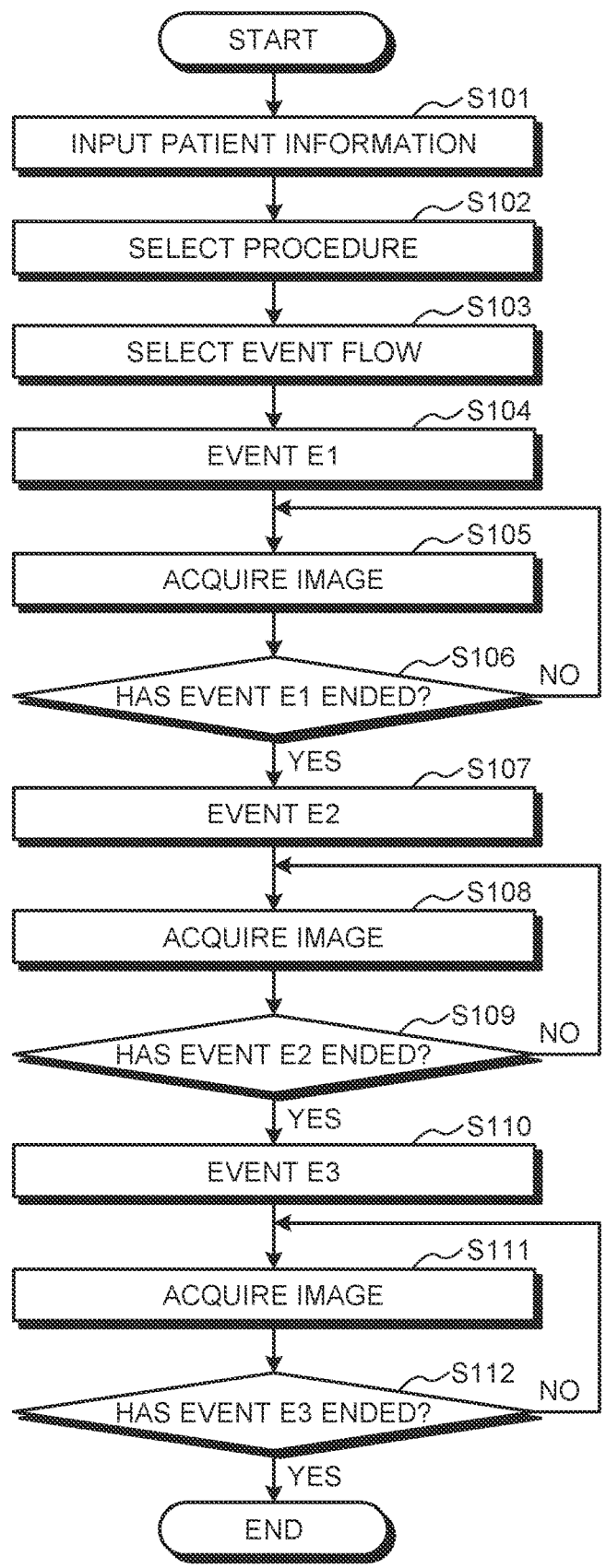

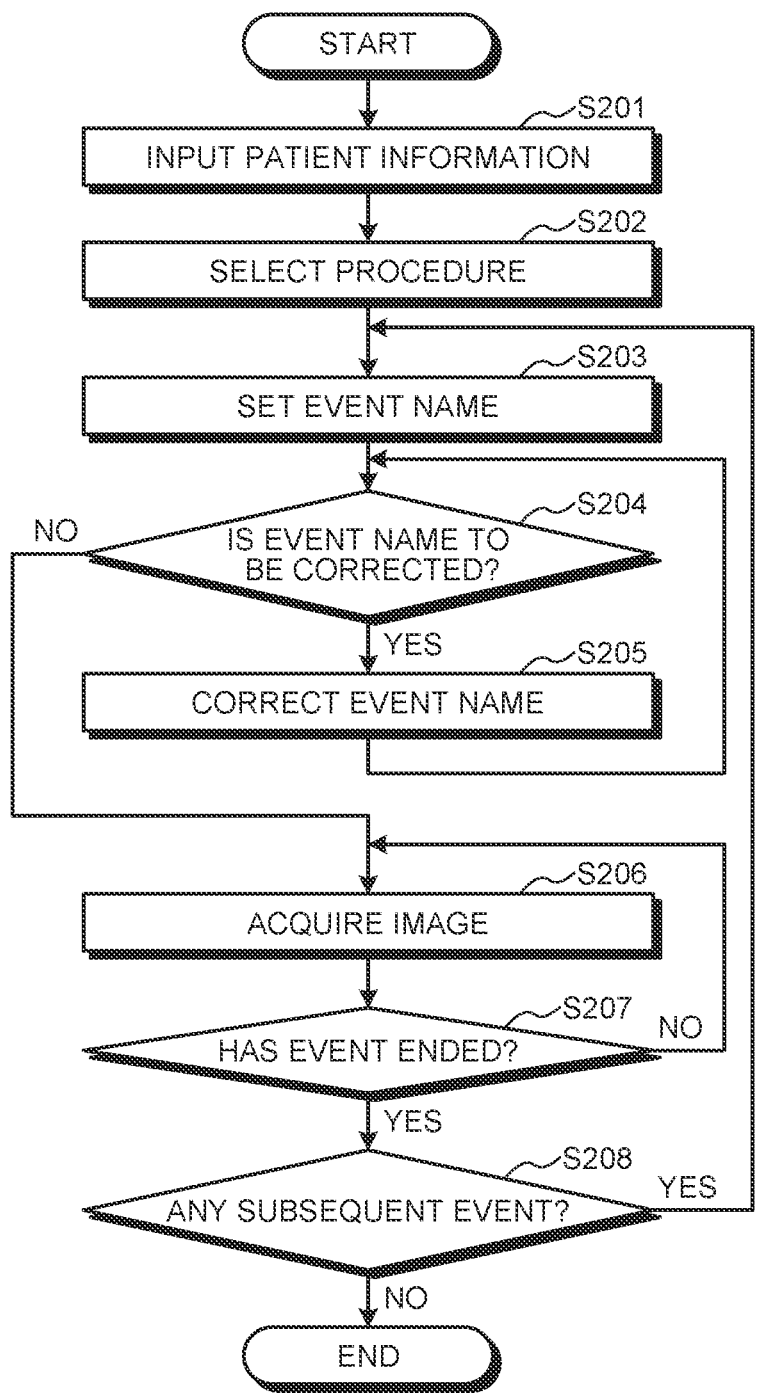

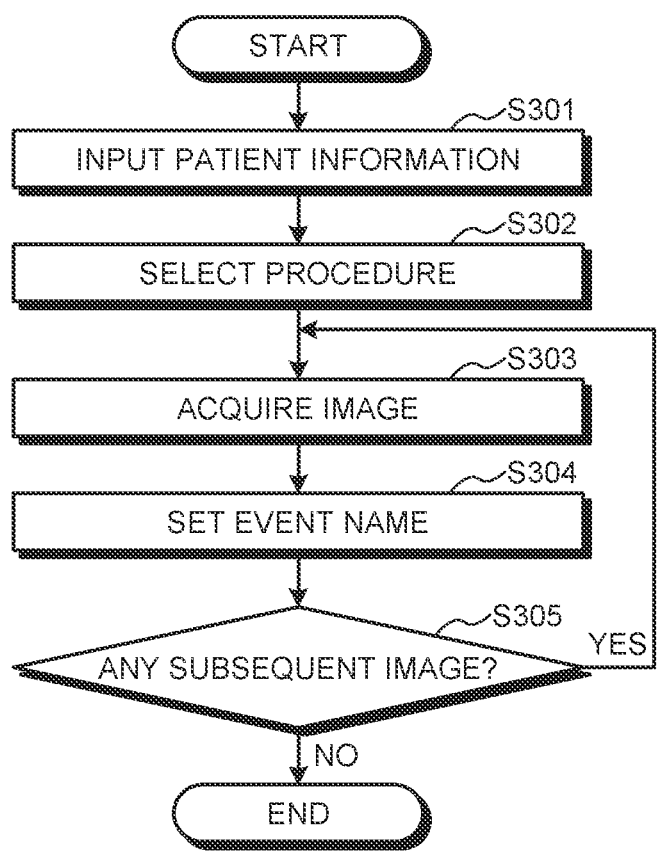

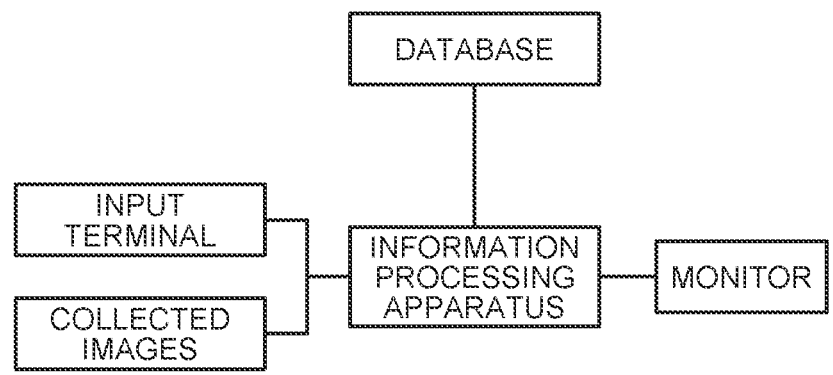
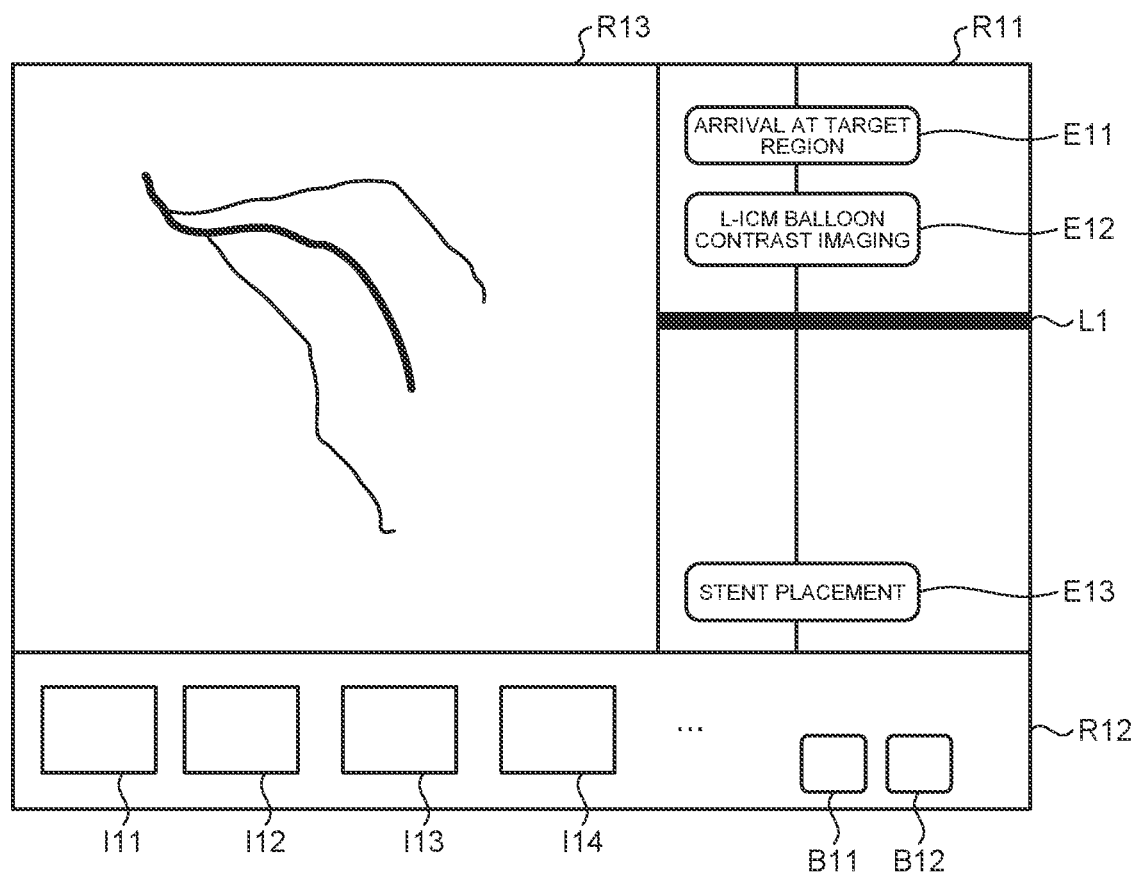

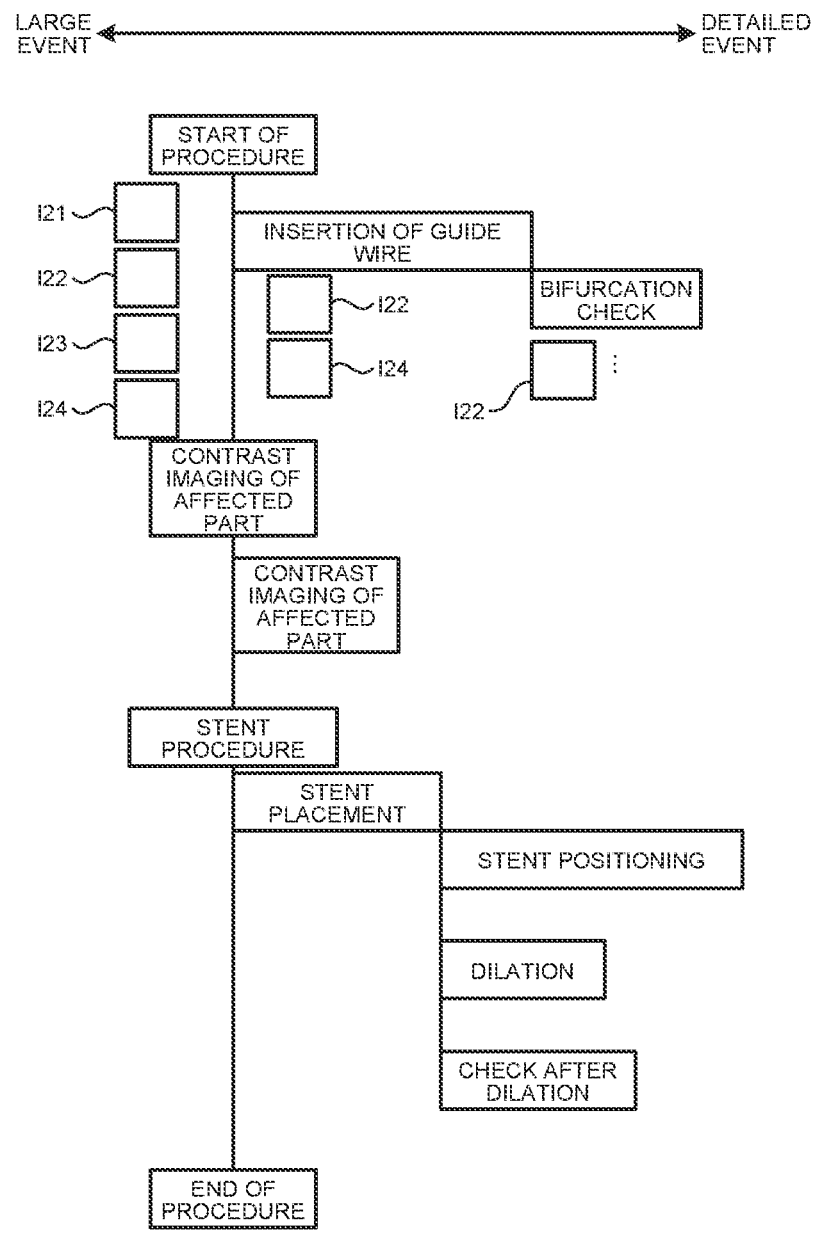

MEDICAL INFORMATION PROCESSING APPARATUS, X-RAY DIAGNOSTIC APPARATUS, AND MEDICAL INFORMATION PROCESSING PROGRAM

CROSS-REFERENCE TO RELATED APPLICATIONS

This application is based upon and claims the benefit of priority from Japanese Patent Application No. 2020-128499, filed on Jul. 29, 2020; the entire contents of which are incorporated herein by reference.

FIELD

Embodiments relate to medical information processing apparatuses, X-ray diagnostic apparatuses, and medical information processing programs.

BACKGROUND

In treatment procedures for subjects, medical images acquired through the treatment procedures are displayed to support users, such as medical doctors who perform the medical procedures. Such medical images are retrieved by the users or other staff, from multiple medical images acquired through the treatment procedures.

BRIEF DESCRIPTION OF THE DRAWINGS

FIG. 3A is a diagram illustrating an example of an event acquiring process according to the first embodiment;

FIG. 3B is a diagram illustrating an example of the event acquiring process according to the first embodiment;

FIG. 3C is a diagram illustrating an example of the event acquiring process according to the first embodiment;

FIG. 6 is a diagram illustrating an example of a related image acquiring process according to the first embodiment;

FIG. 7 is a diagram illustrating an example of display according to the first embodiment;

FIG. 8 is a diagram for explanation of hierarchical display of events according to the first embodiment;

DETAILED DESCRIPTION

Embodiments of a medical information processing apparatus, an X-ray diagnostic apparatus, and a medical information processing program will hereinafter be described in detail while reference is made to the drawings.

First Embodiment

Figure 1:
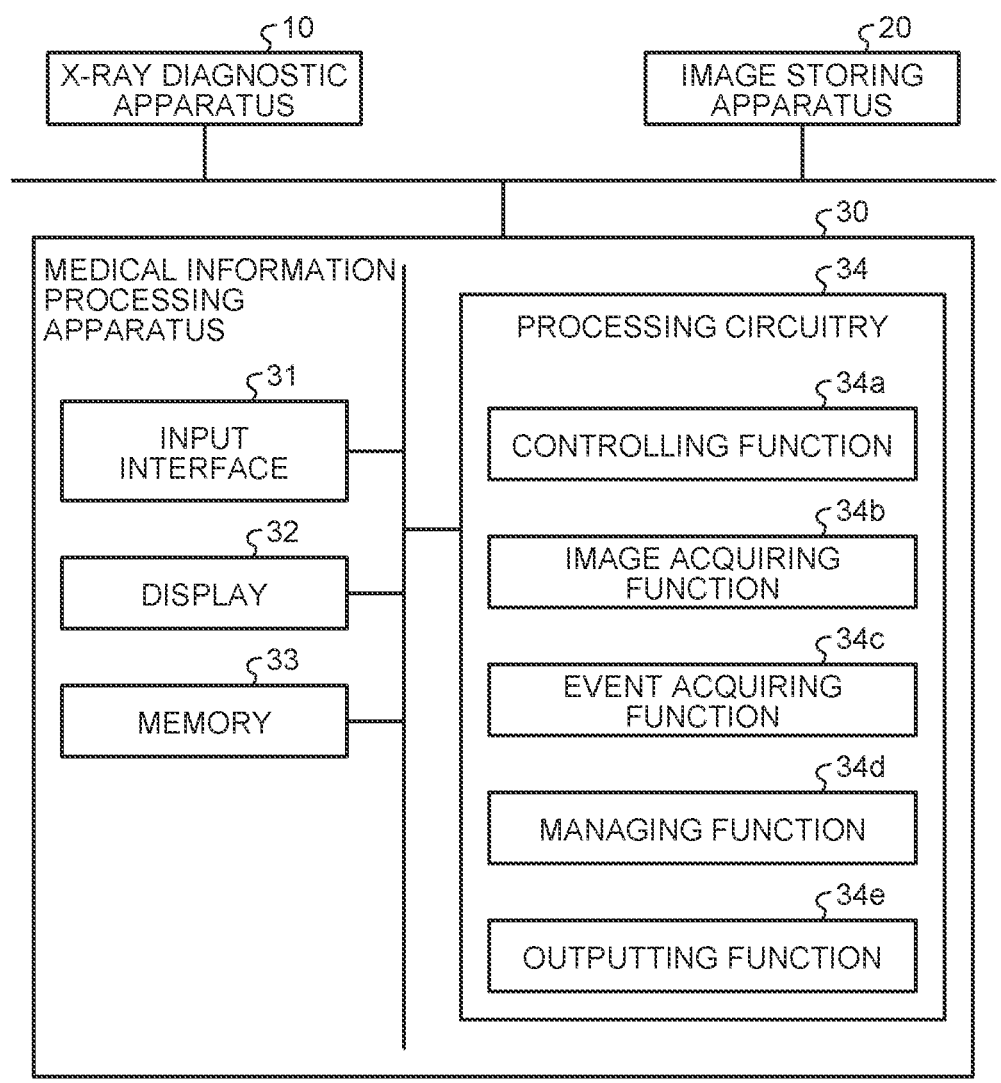
FIG. 1 is a block diagram illustrating an example of a configuration of a medical information processing system according to a first embodiment.

With respect to a first embodiment, a medical information processing system 1 including a medical information processing apparatus 30 will be described as an example. Furthermore, with respect to the first embodiment, X-ray images acquired by an X-ray diagnostic apparatus 10 will be described as an example of medical images. For example, the medical information processing system 1 includes, as illustrated in FIG. 1, the X-ray diagnostic apparatus 10, an image storing apparatus 20, and the medical information processing apparatus 30. FIG. 1 is a block diagram illustrating an example of a configuration of the medical information processing system 1 according to the first embodiment.

As illustrated in FIG. 1, the X-ray diagnostic apparatus 10, the image storing apparatus 20, and the medical information processing apparatus 30 are connected to one another via a network NW. The network NW may be formed of a closed local network in a hospital or may be a network via the Internet. That is, the image storing apparatus 20 may be installed in the same facility as the X-ray diagnostic apparatus 10 and medical information processing apparatus 30, or may be installed in a different facility. However, the medical information processing apparatus 30 is typically placed in an examination room where the X-ray diagnostic apparatus 10 is installed or in an operation room for operating the X-ray diagnostic apparatus 10.

For example, the X-ray diagnostic apparatus 10 sequentially acquires X-ray images during a treatment procedure for a subject P and transmits the acquired X-ray images to the image storing apparatus 20 or the medical information processing apparatus 30. This X-ray diagnostic apparatus 10 will be described later.

The image storing apparatus 20 stores various types of medical images. For example, the image storing apparatus 20 receives and stores the X-ray images acquired by the X-ray diagnostic apparatus 10. The image storing apparatus 20 is a server of a picture archiving and communication system (PACS), for example.

The medical information processing apparatus 30 executes various types of processing based on the X-ray images acquired from the X-ray diagnostic apparatus 10 or image storing apparatus 20. For example, the medical information processing apparatus 30 has, as illustrated in FIG. 1, an input interface 31, a display 32, a memory 33, and processing circuitry 34.

The input interface 31 receives various input operations from a user, converts the input operations received, into electric signals, and outputs the electric signals to the processing circuitry 34. For example, the input interface 31 is implemented by any of: a mouse and a keyboard; a trackball; switches; buttons; a joystick; a touchpad enabling an input operation by a touch on an operation surface; a touch screen having a display screen and a touchpad that have been integrated together; a non-contact input circuit using an optical sensor; and a voice input circuit. The input interface 31 may be formed of a tablet terminal that enables wireless communication with the medical information processing apparatus 30, for example. Furthermore, the input interface 31 may be a circuit that receives an input operation from a user by motion capturing. For example, by processing signals acquired via a tracker or images acquired with respect to a user, the input interface 31 may receive a body motion or line of sight of the user as an input operation. In addition, the input interface 31 does not necessarily include physical operating parts, such as a mouse and a keyboard. For example, examples of the input interface 31 include an electric signal processing circuit that receives an electric signal corresponding to an operation input from an external input device provided separately from the medical information processing apparatus 30 and outputs this electric signal to the processing circuitry 34.

The display 32 displays various types of information. For example, under control of the processing circuitry 34, the display 32 displays X-ray images acquired during a treatment procedure for the subject P. Display of medical images on the display 32 will be described later. Furthermore, for example, the display 32 displays a graphical user interface (GUI) for receiving various instructions and settings, from a user, via the input interface 31. For example, the display 32 is a liquid crystal display or a cathode ray tube (CRT) display. The display 32 may be of the desktop type, or may be formed of, for example, a tablet terminal that enables wireless communication with the medical information processing apparatus 30.

The medical information processing apparatus 30 in FIG. 1 is described herein as including the display 32, but the medical information processing apparatus 30 may include, instead of or in addition to the display 32, a projector. The projector may perform projection on, for example, a screen, a wall, a floor, or a body surface of the subject P, under control of the processing circuitry 34. For example, the projector may also perform projection on, for example, any plane, object, or space, by projection mapping. In addition, the medical information processing apparatus 30 may cause, instead of the display 32, or in addition to the display 32, a display 108 of the X-ray diagnostic apparatus 10 to display an image to be displayed.

The memory 33 is implemented by, for example: a semiconductor memory element, such as a random access memory (RAM) or a flash memory; a hard disk; or an optical disk. For example, the memory 33 stores programs for the circuitry included in the medical information processing apparatus 30 to implement functions of the circuitry. Furthermore, the memory 33 stores X-ray images acquired from the X-ray diagnostic apparatus 10 or image storing apparatus 20. The memory 33 may be implemented by a server group (a cloud) connected to the medical information processing apparatus 30 via the network NW.

The processing circuitry 34 controls the overall operation of the medical information processing apparatus 30 by executing a controlling function 34a, an image acquiring function 34b, an event acquiring function 34c, a managing function 34d, and an outputting function 34e. The image acquiring function 34b is an example of an image acquiring unit. Furthermore, the event acquiring function 34c is an example of an event acquiring unit. The managing function 34d is an example of a managing unit. The outputting function 34e is an example of an output unit.

For example, by reading and executing a program corresponding to the controlling function 34a from the memory 33, the processing circuitry 34 controls various functions including the image acquiring function 34b, the event acquiring function 34c, the managing function 34d, and the outputting function 34e, on the basis of various input operations received from a user via the input interface 31.

Furthermore, for example, by reading and executing a program corresponding to the image acquiring function 34b, the processing circuitry 34 sequentially acquires X-ray images during a treatment procedure for the subject P. In addition, for example, by reading and executing a program corresponding to the event acquiring function 34c, the processing circuitry 34 sequentially acquires events in the treatment procedure on the basis of the X-ray images, during the treatment procedure. Furthermore, for example, by reading and executing a program corresponding to the managing function 34d, the processing circuitry 34 manages the X-ray images and events, in association with temporal information on the treatment procedure. In addition, for example, by reading and executing a program corresponding to the outputting function 34e, the processing circuitry 34 outputs the X-ray images such that relations between the X-ray images and the events are able to be known. Processing by the image acquiring function 34b, the event acquiring function 34c, the managing function 34d, and the outputting function 34e will be described later.

The processing functions are stored in the memory 33 in the medical information processing apparatus 30 illustrated in FIG. 1, the processing functions being in the form of programs executable by a computer. The processing circuitry 34 is a processor that implements the functions corresponding to the programs by reading and executing the programs from the memory 33. In other words, the processing circuitry 34 that has read the programs has the functions corresponding to the read programs.

The controlling function 34a, the image acquiring function 34b, the event acquiring function 34c, the managing function 34d, and the outputting function 34e have been described as being implemented by the single processing circuitry 34 in FIG. 1, but the processing circuitry 34 may be formed of a combination of plural independent processors and each of these processors may implement a function by executing a program. Furthermore, any of the processing functions that the processing circuitry 34 has may be implemented by being distributed to plural pieces of processing circuitry or integrated into single processing circuitry, as appropriate.

In addition, the processing circuitry 34 may implement a function by using a processor of an external device connected via the network NW. For example, by reading and executing the programs corresponding to the respective functions from the memory 33 and using, as a computational resource, a server group (a cloud) connected to the medical information processing apparatus 30 via the network NW, the processing circuitry 34 implements the functions illustrated in FIG. 1.

Figure 2:
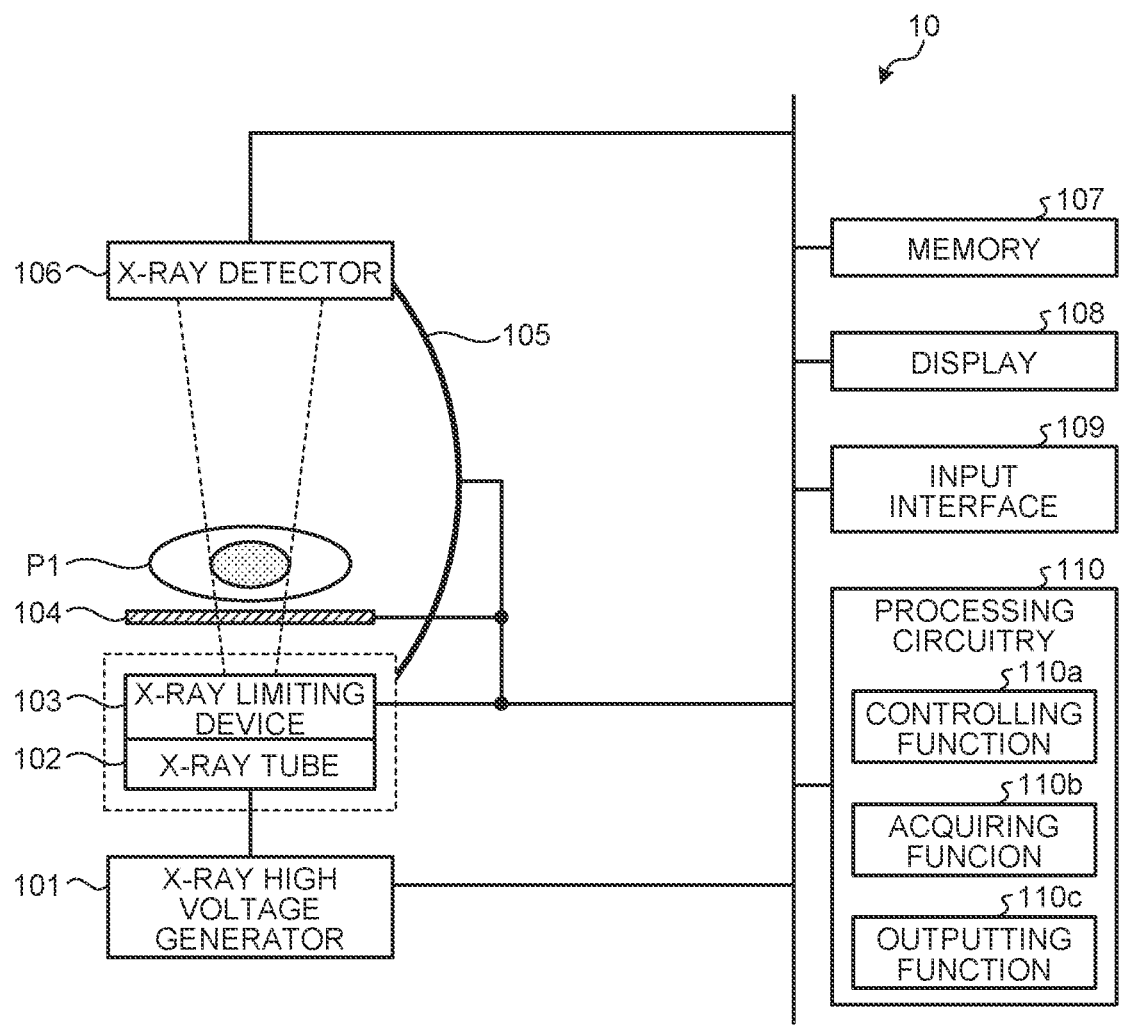
FIG. 2 is a block diagram illustrating an example of a configuration of an X-ray diagnostic apparatus according to the first embodiment.

The X-ray diagnostic apparatus 10 will be described next, using FIG. 2. FIG. 2 is a block diagram illustrating an example of a configuration of the X-ray diagnostic apparatus 10 according to the first embodiment. As illustrated in FIG. 2, the X-ray diagnostic apparatus 10 includes an X-ray high voltage generator 101, an X-ray tube 102, an X-ray limiting device 103, a tabletop 104, a C-arm 105, an X-ray detector 106, a memory 107, the display 108, an input interface 109, and processing circuitry 110.

Under control of the processing circuitry 110, the X-ray high voltage generator 101 supplies high voltage to the X-ray tube 102. For example, the X-ray high voltage generator 101 has: a high voltage generator that has electric circuitry including a transformer and a rectifier and generates high voltage to be applied to the X-ray tube 102; and an X-ray controller that controls output voltage according to X-rays to be emitted by the X-ray tube 102. The high voltage generator may be of the transformer-type or the inverter-type.

The X-ray tube 102 is a vacuum tube having: a cathode (a filament) that generates thermions; and an anode (a target) that receives collision of the thermions and generates X-rays. The X-ray tube 102 generates X-rays by emitting the thermions from the cathode to the anode using the high voltage supplied from the X-ray high voltage generator 101.

The X-ray limiting device 103 has a collimator that narrows the range to be irradiated with the X-rays generated by the X-ray tube 102, and a filter that adjusts the X-rays emitted from the X-ray tube 102.

The collimator in the X-ray limiting device 103 has, for example, four diaphragm blades that are able to be slid. By sliding the diaphragm blades, the collimator narrows the X-rays generated by the X-ray tube 102 and causes the subject P to be irradiated with the X-rays that have been narrowed. The diaphragm blades are plate like members formed of lead, for example, and are provided near an X-ray emission port of the X-ray tube 102, for adjustment of the range to be irradiated with the X-rays.

To reduce the dose of radiation received by the subject P and improve the image quality of X-ray image data, the filter in the X-ray limiting device 103 reduces the soft X-ray components that are easily absorbed into the subject P and/or reduces high energy components that cause reduction in contrast of the X-ray image data, by changing radiation quality of transmitted X-rays by means of the material and/or thickness of the filter. Furthermore, the filter changes the dose of X-rays and the range to be irradiated by means of the material, thickness, and/or position of the filter, for example, to attenuate the X-rays such that the X-rays emitted from the X-ray tube 102 to the subject P have a predetermined distribution.

For example, the X-ray limiting device 103 has a driving system including a motor and an actuator, and controls, under control of the processing circuitry 110 described later, emission of X-rays by operating the driving system. For example, the X-ray limiting device 103 adjusts apertures of the diaphragm blades of the collimator to control the range to be irradiated with the X-rays emitted to the subject P, by applying driving voltage to the driving system according to a control signal received from the processing circuitry 110. Furthermore, for example, the X-ray limiting device 103 adjusts the position of the filter to control the distribution of doses of X-rays emitted to the subject P, by applying driving voltage to the driving system according to a control signal received from the processing circuitry 110.

The tabletop 104 is a bed on which the subject P is laid and the tabletop 104 is placed on a bed unit not illustrated in the drawings. The subject P is not included in the X-ray diagnostic apparatus 10. For example, the bed unit has a driving system including a motor and an actuator, and controls movement and inclination of the tabletop 104 by operating the driving system under control of the processing circuitry 110 described later. The bed unit moves and inclines the tabletop 104, for example, by applying driving voltage to the driving system according to a control signal received from the processing circuitry 110.

The C-arm 105 holds the X-ray tube 102 and X-ray limiting device 103 opposite to the X-ray detector 106, with the subject P interposed therebetween. For example, the C-arm 105 has a driving system including a motor and an actuator, and rotates and moves by operation of the driving system under control of the processing circuitry 110 described later. For example, the C-arm 105 rotates and moves the X-ray tube 102 and X-ray limiting device 103 and the X-ray detector 106, relatively to the subject P to control the X-ray irradiation position and irradiation angle, by applying driving voltage to the driving system according to a control signal received from the processing circuitry 110. The X-ray diagnostic apparatus 10 in FIG. 2 is described herein as a single-plane apparatus as an example, but the embodiment is not limited to this example and the X-ray diagnostic apparatus 10 may be a biplane apparatus.

The X-ray detector 106 is, for example, an X-ray flat panel detector (FPD) having detecting elements arranged in a matrix. The X-ray detector 106 detects X-rays emitted from the X-ray tube 102 and transmitted through the subject P, and outputs a detection signal corresponding to a dose of X-rays detected, to the processing circuitry 110. The X-ray detector 106 may be an indirect conversion detector having a grid, a scintillator array, and an optical sensor array, or a direct conversion detector having a semiconductor element that converts X-rays incident thereon into an electric signal.

The memory 107 is implemented by, for example: a semiconductor memory element, such as a RAM or a flash memory; a hard disk; or an optical disk. For example, the memory 107 stores programs corresponding to various functions read and executed by the processing circuitry 110. The memory 107 may be implemented by a cloud.

The display 108 displays various types of information. For example, under control of the processing circuitry 110, the display 108 displays a GUI for receiving a user's instructions and various X-ray images. For example, the display 108 is a liquid crystal display or a CRT display. The display 108 may be of the desktop type or may be formed of, for example, a tablet terminal enabling wireless communication with the processing circuitry 110.

The X-ray diagnostic apparatus 10 in FIG. 2 is described herein as including the display 108 but the X-ray diagnostic apparatus 10 may include, instead of, or in addition to the display 108, a projector. The projector may perform projection on, for example, a screen, a wall, a floor, or a body surface of the subject P, under control of the processing circuitry 110. For example, the projector may perform projection on any plane, object, or space, by projection mapping.

The input interface 109 receives various input operations from a user, converts the input operations received, into electric signals, and outputs the electric signals to the processing circuitry 110. For example, the input interface 109 is implemented by any of: a mouse and a keyboard; a trackball; switches; buttons; a joystick; a touchpad enabling an input operation by a touch on an operation surface; a touch screen having a display screen and a touchpad that have been integrated together; a non-contact input circuit using an optical sensor; and a voice input circuit. The input interface 109 may be formed of, for example, a tablet terminal that enables wireless communication with the processing circuitry 110. Furthermore, the input interface 109 may be a circuit that receives an input operation from a user by motion capturing. For example, by processing signals acquired via a tracker or images acquired with respect to a user, the input interface 109 may receive a body motion or line of sight of the user as an input operation. In addition, the input interface 109 does not necessarily include physical operating parts, such as a mouse and a keyboard. For example, examples of the input interface 109 include an electric signal processing circuit that receives an electric signal corresponding to an operation input from an external input device provided separately from the X-ray diagnostic apparatus 10 and outputs this electric signal to the processing circuitry 110.

The processing circuitry 110 controls the overall operation of the X-ray diagnostic apparatus 10 by executing a controlling function 110a, an acquiring function 110b, and an outputting function 110c.

For example, by reading and executing a program corresponding to the controlling function 110a from the memory 107, the processing circuitry 110 controls various functions, such as the acquiring function 110b and outputting function 110c, on the basis of various input operations received from a user via the input interface 109.

For example, by reading and executing a program corresponding to the acquiring function 110b from the memory 107, the processing circuitry 110 acquires X-ray images from the subject P. For example, the acquiring function 110b sequentially acquires X-ray images on the basis of X-rays transmitted through the subject P during a treatment procedure for the subject P.

For example, by controlling the X-ray high voltage generator 101 to adjust voltage to be supplied to the X-ray tube 102, the acquiring function 110b controls the dose of X-rays to be emitted to the subject P and performs on-off control. Furthermore, by controlling operation of the X-ray limiting device 103 to adjust the diaphragm blades that the collimator has, the acquiring function 110b controls the range to be irradiated with X-rays emitted to the subject P. In addition, by controlling operation of the X-ray limiting device 103 to adjust the position of the filter, the acquiring function 110b controls the distribution of doses of X-rays. Furthermore, by controlling operation of the C-arm 105 to change the position and angle of the C-arm 105 relatively to the subject P, the acquiring function 110b controls the imaging position and imaging angle. The position and angle of the C-arm 105 are also referred to herein as arm position information. In addition, the acquiring function 110b generates X-ray images on the basis of detection signals received from the X-ray detector 106 and stores the generated X-ray images into the memory 107.

Furthermore, by reading and executing a program corresponding to the outputting function 110c from the memory 107, the processing circuitry 110 controls transmission and reception of data via the network NW and display at the display 32. For example, the outputting function 110c transmits the X-ray images acquired by the acquiring function 110b to the medical information processing apparatus 30 via the network NW and causes the display 32 to display the X-ray images. In addition, for example, the outputting function 110c causes the display 32 to display a GUI for receiving input operations from a user.

The processing functions have been stored in the memory 107 of the X-ray diagnostic apparatus 10 illustrated in FIG. 2, the processing functions being in the form of programs executable by a computer. The processing circuitry 110 is a processor that implements functions corresponding to the programs by reading and executing the programs from the memory 107. In other words, the processing circuitry 110 that has read the programs has the functions corresponding to the read programs.

The controlling function 110a, the acquiring function 110b, and the outputting function 110c have been described as being implemented by the single processing circuitry 110 in FIG. 2, but the processing circuitry 110 may be formed of a combination of plural independent processors and the functions may be implemented by the processors executing the programs. Furthermore, any of the processing functions that the processing circuitry 110 has may be implemented by being distributed to plural pieces of processing circuitry or integrated into single processing circuitry.

In addition, the processing circuitry 110 may implement a function by using a processor of an external device connected via the network NW. For example, by reading and executing the programs corresponding to the respective functions from the memory 107 and using, as a computational resource, a server group (a cloud) connected to the X-ray diagnostic apparatus 10 via the network NW, the processing circuitry 110 implements the functions illustrated in FIG. 2.

The above description is on the medical information processing system 1 including the X-ray diagnostic apparatus 10, the image storing apparatus 20, and the medical information processing apparatus 30. The following description is on processing performed in the medical information processing system 1.

For example, the X-ray diagnostic apparatus 10 sequentially acquires X-ray images from the subject P in a treatment procedure for the subject P. Furthermore, the medical information processing apparatus 30 sequentially acquires the X-ray images from the X-ray diagnostic apparatus 10 and causes the display 32 to sequentially display the acquired X-ray images in real time. A user is thereby able to check, for example, a structure in the body of the subject P and a medical device inserted in the body of the subject P, and also able to proceed smoothly with the treatment procedure. That is, by acquiring and displaying X-ray images, the medical information processing system 1 is able to support a user (a medical doctor in attendance) who conducts a treatment procedure.

A treatment procedure is often executed by a team of people including a medical doctor in attendance, and a member other than the medical doctor in attendance may want to know the current situation in the treatment procedure by referring to real-time X-ray images. Furthermore, during execution of a treatment procedure, a medical doctor in attendance or another member may refer to an X-ray image that has been acquired in the treatment procedure.

However, characteristics specific to the current situation in a treatment procedure may not necessarily be represented by real-time X-ray images and the process leading to the current situation may be difficult to be determined just from the real-time X-ray images. Therefore, even if a member in a team refers to real-time X-ray images in a treatment procedure, the member may be unable to know the current situation in the treatment procedure and communication in the team may thus be made difficult. Furthermore, for example, in a case where a member in a team attempts to display an X-ray image that has been acquired in a treatment procedure on the display 108 as a reference image during execution of the treatment procedure, finding the image needed may be troublesome.

The medical information processing apparatus 30 thus enables effective utilization of medical images, such as X-ray images, by means of processing by the processing circuitry 34. The processing executed by the processing circuitry 34 will be described in detail below.

Firstly, the image acquiring function 34b sequentially acquires X-ray images during a treatment procedure for the subject P. The image acquiring function 34b may acquire the X-ray images via the image storing apparatus 20, or may acquire the X-ray images directly from the X-ray diagnostic apparatus 10. Furthermore, the event acquiring function 34c sequentially acquires events in the treatment procedure during the treatment procedure.

Examples of an event acquiring process by the event acquiring function 34c will now be described using FIG. 3A, FIG. 3B, and FIG. 3C. FIG. 3A, FIG. 3B, and FIG. 3C are diagrams illustrating examples of an event acquiring process according to the first embodiment.

FIG. 3A will be described firstly. In the case illustrated in FIG. 3A, before a treatment procedure is starred, the event acquiring function 34c receives input of patient information (Step S101) and receives a selection of a procedure (Step S102). For example, the event acquiring function 34c may execute Step S101 and Step S102 by receiving an input operation from a user via the input interface 31. Step S101 and Step S102 may be omitted as appropriate.

Furthermore, the event acquiring function 34c receives a selection of an event flow (Step S103). A case where an event flow including an event E1, an event E2, and an event E3 has been selected will be described as an example with respect to FIG. 3A. For example, the event acquiring function 34c may execute Step S103 by receiving an input operation from a user via the input interface 31. The memory 33 may store a database including plural types of event flows beforehand, and the event acquiring function 34c may receive an operation from a user, the operation being for selecting any one of the event flows from that database, for example. Or, on the basis of the patient information received at Step S101 and/or the procedure selected at Step S102, the event acquiring function 34c may automatically select an event flow.

After Step S103, the event acquiring function 34c determines that the treatment procedure is in a situation of the first event E1 (Step S104). Furthermore, after the treatment procedure is started, the image acquiring function 34b acquires X-ray images acquired at the X-ray diagnostic apparatus 10 (Step S105). The event acquiring function 34c may acquire the event E1 for the X-ray images acquired at Step S105.

Furthermore, the managing function 34d manages the X-ray images acquired at Step S105 and the event E1, in association with temporal information on the treatment procedure. For example, the managing function 34d stores the X-ray images acquired at Step S105 with supplementary information added to the X-ray images, the supplementary information being the event E1 and the temporal information. The managing function 34d stores the event E1 and the temporal information in Digital Imaging and Communications in Medicine (DICOM) tags of the X-ray images. The temporal information may be information on dates and times on and at which the X-ray images were acquired at the X-ray diagnostic apparatus 10, or may be information on dates and times on and at which the medical information processing apparatus 30 acquired the X-ray images from the X-ray diagnostic apparatus 10. Furthermore, the managing function 34d may further store, as the supplementary information on the X-ray images, the patient information received at Step S101 or the procedure selected at Step S102.

Subsequently, the event acquiring function 34c determines whether or not the event E1 has ended (Step S106) and if the event E1 has not ended (No at Step S106), the event acquiring function 34c proceeds to Step S105 again. For example, on the basis of the X-ray images acquired, the event acquiring function 34c automatically determines whether or not the event E1 has ended. If, for example, the event E1 is an event where "a medical device is inserted from the femoral region of the subject P and caused to reach the heart that is a region to be treated", the event acquiring function 34c may automatically determine whether or not the event E1 has ended on the basis of a positional relation between the medical device and the heart of the subject P that appear in an X-ray image. If the event E1 has not ended, the event acquiring function 34c proceeds to Step S105 again and acquires the event E1 for X-ray images newly acquired. That is, the event acquiring function 34c may acquire an event on the basis of X-ray images. Therefore, even if the X-ray images themselves do not represent characteristics specific to the event E1, information on the event E1 may be assigned to the X-ray images.

Or, by comparing positional information on a peripheral device with a database, the event acquiring function 34c may automatically determine whether or not the event E1 has ended. For example, if the C-arm 105 is moved to follow the position of the distal end of the medical device, the event acquiring function 34c may automatically determine whether or not the event E1 has ended on the basis of positional information on the C-arm 105. Or, by receiving an input operation from a user via the input interface 31, the event acquiring function 34c may determine whether or not the event E1 has ended.

On the contrary, if the event E1 has ended (Yes at Step S106), the event acquiring function 34c determines that the treatment procedure has proceeded to be in a situation of the event E2 (Step S107). Furthermore, the image acquiring function 34b acquires X-ray images acquired at the X-ray diagnostic apparatus 10 (Step S108). The event acquiring function 34c may acquire the event E2 for the X-ray images acquired at Step S108. For example, the event acquiring function 34c determines whether or not the event E1 has ended on the basis of the X-ray images acquired at Step S105 and if the event E1 has ended, the event acquiring function 34c determines that the treatment procedure has proceeded to be in the situation of the event E2 and acquires the event E2 for the X-ray images newly acquired at Step S108. Furthermore, the managing function 34d manages the X-ray images acquired at Step S108 and the event E2, in association with temporal information on the treatment procedure. The determination of the end of the event E1 at Step S106 may be executed by detecting characteristics specific to the end of the event E1 or may be executed by determining start of the event E2 through detection of characteristics specific to the event E2. This method of determination is similarly applicable to Step S109 and so on.

Subsequently, the event acquiring function 34c determines whether or not the event E2 has ended (Step S109) and if the event E2 has not ended (No at Step S109), the event acquiring function 34c proceeds to Step S108 again. For example, the event acquiring function 34c determines whether or not the event E2 has ended on the basis of the X-ray images, and if the event E2 has not ended, the event acquiring function 34c proceeds to Step S108 again and acquires the event E2 for X-ray images newly acquired. On the contrary, if the event E2 has ended (Yes at Step S109), the event acquiring function 34c determines that the treatment procedure has proceeded to be in a situation of the event E3 (Step S110). Furthermore, the image acquiring function 34b acquires X-ray images acquired at the X-ray diagnostic apparatus 10 (Step S111). The event acquiring function 34c may acquire the event E3 for the X-ray images acquired at Step S111. For example, the event acquiring function 34c determines whether or not the event E2 has ended on the basis of the X-ray images acquired at Step S108, and if the event E2 has ended, the event acquiring function 34c determines that the treatment procedure has proceeded to be in the situation of the event E3 and acquires the event E3 for the X-ray images newly acquired at Step S111. Furthermore, the managing function 34d manages the X-ray images acquired at Step S111 and the event E3, in association with temporal information on the treatment procedure.

Subsequently, the event acquiring function 34c determines whether or not the event E3 has ended (Step S112) and if the event E3 has not ended (No at Step S112), the event acquiring function 34c proceeds to Step S111 again. For example, the event acquiring function 34c determines whether or not the event E3 has ended on the basis of the X-ray images, and if the event E3 has not ended, the event acquiring function 34c proceeds to Step S111 again and acquires the event E3 for X-ray images newly acquired. On the contrary, if the event E3 has ended (Yes at Step S112), the event acquiring function 34c ends the process.

That is, according to the process illustrated in FIG. 3A, the image acquiring function 34b sequentially acquires X-ray images during a treatment procedure for the subject P and the event acquiring function 34c sequentially acquires events in the treatment procedure during the treatment procedure. That is, on the basis of the X-ray images sequentially acquired, the event acquiring function 34c sequentially identifies images in which the events occurred, from the X-ray images sequentially acquired. For example, by determining whether or not each event included in an event flow has ended on the basis of the X-ray images, the event acquiring function 34c may sequentially acquire events for X-ray images newly acquired. Furthermore, the managing function 34d may manage the X-ray images and events, in association with temporal information on the treatment procedure. That is, the managing function 34d stores medical images acquired and also stores information on events that occurred, in association with images identified as images in which the events occurred, the images being from the medical images stored.

FIG. 3B will be described next. In the case illustrated in FIG. 3B, before a treatment procedure is started, the event acquiring function 34c receives input of patient information (Step S201) and receives a selection of a procedure (Step S202). For example, the event acquiring function 34c may execute Step S201 and Step S202 by receiving an input operation from a user via the input interface 31. Step S201 and Step S202 may be omitted as appropriate.

Furthermore, the event acquiring function 34c sets an event name. For example, after Step S202, the event acquiring function 34c sets the first event name for the treatment procedure (Step S203). The event acquiring function 34c may set the event name by receiving an input operation from a user via the input interface 31, for example. For example, the event acquiring function 34c may set the event name by voice input. Or, on the basis of the patient information received at Step S201 and/or the procedure selected at Step S202, the event acquiring function 34c may automatically set the event name.

Subsequently, the event acquiring function 34c determines whether or not the event name is to be corrected (Step S204). For example, in a case where a plan has been changed or automatic recognition and a user's recognition are in disagreement, the event acquiring function 34c may determine that the event name is to be corrected (Yes at Step S204) and correct the event name (Step S205). The event acquiring function 34c may correct the event name by receiving an input operation from a user or automatically reset the event name.

On the contrary, if the event name is not to be corrected (No at Step S204), the image acquiring function 34b acquires X-ray images acquired at the X-ray diagnostic apparatus 10 (Step S206). The event acquiring function 34c may acquire the event name set at Step S203 or corrected at Step S205, for the X-ray images acquired at Step S206. Furthermore, the managing function 34d may manage the X-ray images and event, in association with temporal information on the treatment procedure.

Subsequently, the event acquiring function 34c determines whether or not the event having the event name set at Step S203 or corrected at Step S205 has ended (Step S207), and if the event has not ended (No at Step S207), the event acquiring function 34c proceeds to Step S206 again. For example, on the basis of the X-ray images acquired, the event acquiring function 34c automatically determines whether or not the event has ended. If the event has not ended, the event acquiring function 34c proceeds to Step S206 again and acquires the event having the event name set at Step S203 or corrected at Step S205 for X-ray images newly acquired. That is, the event acquiring function 34c may acquire an event on the basis of X-ray images.

Or, at Step S207, by comparing positional information on a peripheral device with a database, the event acquiring function 34c may automatically determine whether or not the event has ended. Furthermore, by receiving an input operation from a user via the input interface 31, the event acquiring function 34c may determine whether or not the event has ended.

On the contrary, if the event has ended (Yes at Step S207), the event, acquiring function 34c determines whether or not there is any subsequent event (Step S208). If there is any subsequent event (Yes at Step S208), the event acquiring function 34c proceeds to Step S203 again and sets an event name for the subsequent event. On the contrary, if there is no subsequent event (No at Step S208), the event acquiring function 34c ends the process.

That is, according to the process illustrated in FIG. 3B, the image acquiring function 34b sequentially acquires X-ray images during a treatment procedure for the subject P and the event acquiring function 34c sequentially acquires events in the treatment procedure during the treatment procedure. For example, by determining whether or not an event having an event name set at Step S203 or corrected at Step S205 has ended on the basis of X-ray images, the event acquiring function 34c may sequentially acquire events for X-ray images newly acquired. Furthermore, the managing function 34d may manage the X-ray images and events, in association with temporal information on the treatment procedure.

FIG. 3C will be described next. In the case illustrated in FIG. 3C, before a treatment procedure is started, the event acquiring function 34c receives input of patient information (Step S301) and receives a selection of a procedure (Step S302). For example, the event acquiring function 34c may execute Step S301 and Step S302 by receiving an input operation from a user via the input interface 31. Step S301 and Step S302 may be omitted as appropriate.

Subsequently, the image acquiring function 34b acquires X-ray images acquired at the X-ray diagnostic apparatus 10 (Step S303). Next, the event acquiring function 34c sets an event name by a process using the X-ray images acquired at Step S303 (Step S304). For example, the event acquiring function 34c detects a medical device from the X-ray images acquired at Step S303 and identifies the type of the medical device detected and the position of the medical device in the body of the subject P. In a case where a balloon used to dilate a stenotic portion of a blood vessel is detected as a medical device and dilation of that balloon is detected in each of consecutive frames, for example, the event acquiring function 34c may acquire an event, "Balloon dilation". That is, the event acquiring function 34c may acquire an event on the basis of X-ray images. Furthermore, the managing function 34d may manage the X-ray images and event, in association with temporal information on the treatment procedure.

Subsequently, the event acquiring function 34c determines whether or not there is any subsequent X-ray image (Step S305) and if there is any subsequent X-ray image (Yes at Step S305), the event acquiring function 34c proceeds to Step S303 again. On the contrary, if there is no subsequent X-ray image (No at Step S305), the event acquiring function 34c ends the process. That is, according to the process illustrated in FIG. 3C, the image acquiring function 34b may sequentially acquire X-ray images during a treatment procedure for the subject P, the event acquiring function 34c may sequentially acquire events in the treatment procedure during the treatment procedure on the basis of the X-ray images, and the managing function 34d may manage the X-ray images and event, in association with temporal information on the treatment procedure.

FIG. 3A, FIG. 3B, and FIG. 3C are just examples, and the event acquiring function 34c may acquire events by any of various methods. For example, the event acquiring function 34c may acquire events on the basis of images acquired by a medical diagnostic imaging device (a modality) different from the X-ray diagnostic apparatus 10. For example, at Step S304 in FIG. 3C, the event acquiring function 34c may set an event name on the basis of ultrasound images acquired in parallel with the X-ray images.

Figure 4:
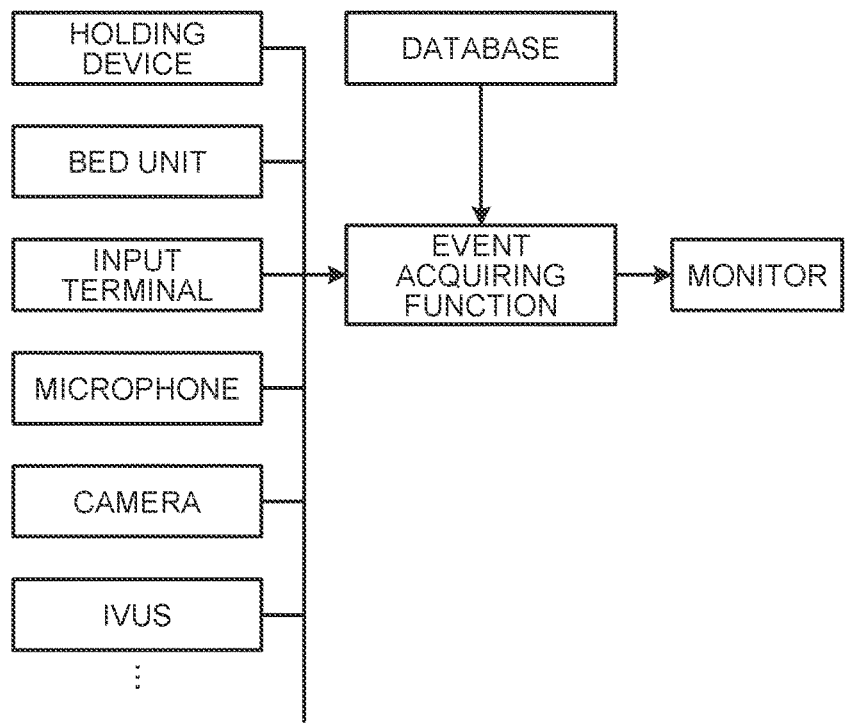
FIG. 4 is a diagram illustrating an example of the event acquiring process according to the first embodiment.

As illustrated in FIG. 4, for example, the event acquiring function 34c may execute any of the various event acquiring methods described above, on the basis of a database storing event types. This database is managed in the memory 33, for example, and may be read therefrom as appropriate. For example, the event acquiring function 34c compares any of various types of information with event names registered in the database and acquires any matching or similar event name, the various types of information including control information on a holding device or bed unit, input information from an input terminal, input information from a microphone or a camera, and ultrasound images acquired by intravascular ultrasonography (IVUS). The holding device in FIG. 4 is, for example, the C-arm 105 illustrated in FIG. 2. Furthermore, the bed unit in FIG. 4 is, for example, a device that controls movement and inclination of the tabletop 104 illustrated in FIG. 2. Furthermore, the input terminal in FIG. 4 is an example of the input interface 31 illustrated in FIG. 1 and is, for example, a mouse and a keyboard. In addition, the microphone and camera in FIG. 4 are an example of the input interface 31 illustrated in FIG. 1. Furthermore, the ultrasound images by IVUS are managed in the memory 33, for example, and may be read therefrom as appropriate. That is, by registering event names in the database beforehand and acquiring an event using the database, the event acquiring function 34c acquires the same event name for events of the same type and is thus able to manage events efficiently. FIG. 4 is a diagram illustrating an example of the event acquiring process according to the first embodiment.

Next, the outputting function 34e outputs X-ray images such that relations between the X-ray images and events are able to be known. For example, on the basis of temporal information associated with the X-ray images and events, the outputting function 34e displays a timeline having the events arranged chronologically, on the display 32. Furthermore, the outputting function 34e displays the X-ray images on the display 32 such that chronological relations between the X-ray images and the events displayed in the timeline are able to be known.

Figure 5:
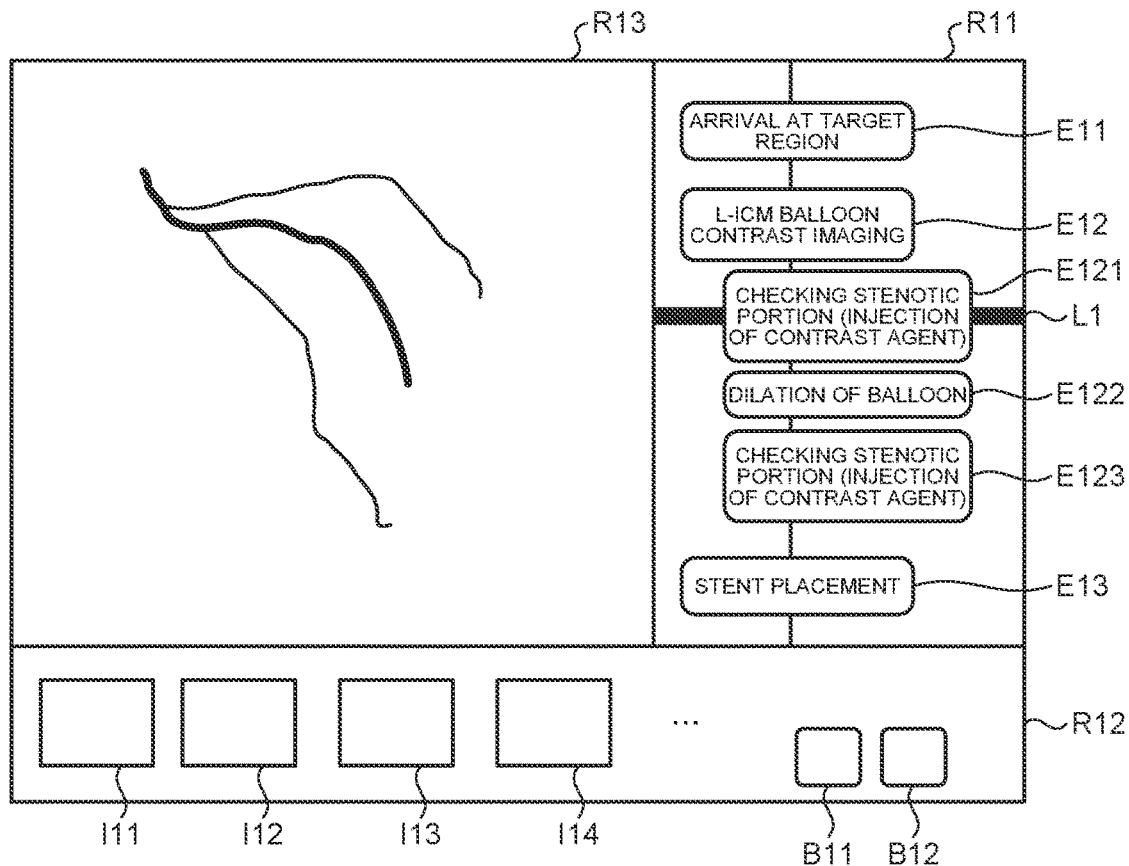
FIG. 5 is a diagram illustrating an example of display according to the first embodiment.

For example, the outputting function 34e displays a display screen including an area R11, an area R12, and an area R13, as illustrated in FIG. 5, on the display 32. The outputting function 34e displays the display screen in FIG. 5 on the display 32 during a treatment procedure, for example. FIG. 5 is a diagram illustrating an example of display according to the first embodiment.

Specifically, the outputting function 34e displays a timeline having event arranged chronologically, in the area R11. FIG. 5 illustrates a case where, for example, an event E11 (Arrival at target region), an event E12 (L-ICM balloon contrast imaging), and an event E13 (Stent placement) are displayed in a timeline. Furthermore, FIG. 5 illustrates that the event E12 is formed of detailed events, such as an event E121 (Checking stenotic portion (injection of contrast agent)), an event E122 (Dilation of balloon), and an event E123 (Checking stenotic portion (injection of contrast agent)).

In addition, the outputting function 34e displays the current event with a line L1 in the area R11. That is, in FIG. 5, the event E12 including the event E121 is the current event, the event E11 is a past event, and the event E13 is a subsequent event. Furthermore, the outputting function 34e may display X-ray images associated with the event E121 in the area R12 or the area R13. For example, the outputting function 34e displays, as a thumbnail, an X-ray image I11 acquired while the event E121 was occurring, in the area R12 and also displays the X-ray image I11 enlarged in the area R13. That is, by displaying the line L1 on the timeline, the outputting function 34e may display the X-ray image I11 such that chronological relations between the X-ray image I11 and the events displayed in the timeline are able to be known. For example, by referring to the display in FIG. 5, members of a team for a treatment procedure are able to know the current situation of the treatment procedure and readily communicate with each other.

The outputting function 34e may display all of the events included in the treatment procedure or may display only some of the events. For example, the outputting function 34e may select events to be displayed on the basis of a list of events to be displayed, and not display any event not included in this list. The outputting function 34e is thereby able to reduce the number of events to be displayed and prevent a user from getting confused by display of too much information.

Furthermore, the line L1 is described herein to indicate the current event, but the line L1 may be movable on the timeline in any way. For example, during a treatment procedure, a user may move the line L1 to the position of the event E11 that is a past event. In this case, the outputting function 34e displays, on the display 32, X-ray images associated with the event E11 at which the line L1 that has been moved is positioned. Candidates are thereby able to be narrowed down using information on a situation in a treatment procedure in a case where X-ray images that have been acquired are displayed as reference images during execution of the treatment procedure, and the trouble to search for images needed is thus able to be reduced.

The outputting function 34e may further display, in addition to an X-ray image associated with an event at which the line L1 is positioned, a related image that is related to that X-ray image. For example, in a case where the line L1 is positioned at the event E121 as illustrated in FIG. 5, the outputting function 34e may display, in addition to the X-ray image I11 associated with the event E121, related images, such as an image I12, an image I13, and an image I14, in the area R12. Furthermore, in a case where any of these related images is selected by a user, the outputting function 34e may display that related image enlarged in the area R13.

The related images related to the X-ray image I11 are, for example, images having supplementary information that is the same as or similar to that of the X-ray image I11. For example, the outputting function 34e retrieves any medical image having supplementary information, such as patient information or an event, from medical images stored in the memory 33 or image storing apparatus 20, the supplementary information being similar to that of the X-ray image I11, and displays that medical image as a related image on the display 32. The outputting function 34e displays, for example, an X-ray image acquired from the subject P in the event E11 that is a past event, as a related image related to the X-ray image I11, on the display 32.

Furthermore, for example, a related image related to the X-ray image I11 is an image having image features that are similar to those of the X-ray image I11. The outputting function 34e retrieves an image having a medical device appearing in the image, the medical device being the same as or similar to that in the X-ray image I11 or an image acquired for an organ that is the same as that in the X-ray image I11, from medical images stored in the memory 33 or image storing apparatus 20, and displays that image as a related image on the display 32, for example.

Furthermore, for example, a related image related to the X-ray image I11 is an X-ray image having arm position information that is the same as or similar to that of the X-ray image I11. That is, the outputting function 34e retrieves an X-ray image having an imaging position and an imaging angle that are the same as or similar to those of the X-ray image I11 from medical images stored in the memory 33 or image storing apparatus 20, and displays that X-ray image as a related image, on the display 32. The outputting function 34e is thereby able to narrow down related images to be displayed to those near the real-time arm angle, in a case where display is performed during a treatment procedure, for example.

In a case where a related image is selected on the basis of arm position information, any X-ray image having dissimilar arm position information is excluded. The outputting function 34e may notify a user of the fact that there is an X-ray image for which display has been omitted because of its dissimilar arm position information. For example, the outputting function 34e may display text on the timeline, the text indicating that there is an X-ray image for which display has been omitted because of its dissimilar arm position information.

Furthermore, a related image related to the X-ray image I11 may be a processed image generated on the basis of the X-ray image I11. For example, the outputting function 34e may retrieve a parametric imaging (PI) image generated on the basis of the X-ray image I11, from medical images stored in the memory 33 or image storing apparatus 20, and display, on the display 32, the PI image as a related image related to the X-ray image I11. The PI image is a color image generated by calculating a parameter, such as a bloodstream arrival time from X-ray images corresponding to plural frames resulting from contrast imaging of a blood vessel and assigning a color according to a value of the parameter to each pixel.

The outputting function 34e may read a processed image that has been generated or read an application that has been used to generate a processed image. For example, the outputting function 34e may read a PI image stored in the memory 33 or image storing apparatus 20 or read an application used to generate a PI image. In the case where the outputting function 34e reads the application, the outputting function 34e may generate the PI image from X-ray images corresponding to plural frames including the X-ray image I11 and display the PI image as a related image on the display 32, for example.

Furthermore, the outputting function 34e may process or generate and display a related image according to the X-ray image I11. For example, in a case where the outputting function 34e has read a PI image based on the X-ray image I11, the outputting function 34e may display the PI image as a related image after processing the display mode, such as the window level (WL) or window width (WW), of the PI image to facilitate comparison between the X-ray image I11 and the PI image. Furthermore, for example, in a case where the outputting function 34e has read an application used to generate a PI image, the outputting function 34e may generate the PI image by setting the WL or WW to facilitate comparison between the X-ray image I11 and the PI image and display the PI image as a related image.

Although PI images have been described as an example of processed images generated on the basis of the X-ray image I11, the embodiment is not limited to this example. For example, the outputting function 34e may display, as a related image related to the X-ray image I11, a blood vessel wall image having only a blood vessel wall extracted from the X-ray image I11, or a sketch image having a guide line marked on the X-ray image I11, on the display 32. Furthermore, for example, the outputting function 34e may display, as a related image related to the X-ray image I11, an image having a blood vessel wall image or sketch image and the X-ray image III superimposed on each other, the blood vessel wall image or sketch image having been generated on the basis of an X-ray image acquired before the X-ray image I11, on the display 32.

The outputting function 34e may display a processed image near the original image. For example, the outputting function 34e may display a processed image generated on the basis of the X-ray image I11 at a position adjacent to the X-ray image I11 on a timeline. Or, the outputting function 34e may display a processed image at a position corresponding to the date and time on and at which the processed image was generated, on a timeline.

Furthermore, a related image related to the X-ray image I11 is not necessarily an X-ray image, and may be an image acquired using an apparatus different from the X-ray diagnostic apparatus 10. For example, the outputting function 34e may display, as a related image related to the X-ray image I11, an ultrasound image acquired while the event E121 was occurring, on the display 32. Furthermore, for example, the outputting function 34e may display, as a related image, an ultrasound image acquired in the past from the subject P, on the display 32. The outputting function 34e may display, as a related image, an IVUS image or transesophageal echocardiography (TEE) image acquired from the subject P, on the display 32, for example. In addition, the outputting function 34e may display, as a related image, any of various medical images, such as an X-ray computed tomography (CT) image, a magnetic resonance imaging (MRI) image, a single photon emission computed tomography (SPECT) image, a positron emission computed tomography (PET) image, and an optical coherence tomography (OCT) image, on the display 32.

Furthermore, a related image related to the X-ray image I11 may be a two-dimensional medical image generated from a three-dimensional medical image. For example, the outputting function 34e may generate a two-dimensional medical image by rendering processing of a three-dimensional medical image, such as a preoperative CT image or cone-beam computed tomography (CBCT) image, and display the two-dimensional medical image as a related image on the display 32. The outputting function 34e may generate a two-dimensional medical image on the basis of arm position information added to the X-ray image I11. That is, the outputting function 34e my generate, as a related image related to the X-ray image I11, a two-dimensional medical image having an imaging position and an imaging angle made to approximate those of the X-ray image I11 and display the two-dimensional medical image on the display 32. The outputting function 34e is thereby able to narrow down related images to be displayed to those near the real-time arm angle, in a case where display is performed during a treatment procedure, for example.

There are plural types of related images as described above, and the outputting function 34e may thus narrow down related images to be displayed on the basis of an instruction from a user. For example, as illustrated in FIG. 5, the outputting function 34e may cause an icon B11 and an icon B12 to be displayed, and narrow down related images to be displayed, according to an operation on these icons. For instance, the icon B11 corresponds to "Ultrasound image". When a user performs an operation on the icon B11, the outputting function 34e may select whether or not to display an ultrasound image as a related image related to the X-ray image I11.

For example, as illustrated in FIG. 6, the outputting function 34e may retrieve a related image using a database. For example, the event acquiring function 34c may perform a search in the database on the basis of a keyword input from an input terminal, supplementary information added to a acquired image, such as the X-ray image I11, or image features of a acquired image, and display the retrieved related image related to the acquired image, on a monitor, such as the display 32. FIG. 6 is a diagram illustrating an example of a related image acquiring process according to the first embodiment.

Furthermore, in FIG. 5, the detailed events (the event E121, the event E122, and the event E123) included in the event E12 have been described to be displayed also, but as illustrated in FIG. 7, the outputting function 34e may omit the display of these detailed events. That is, the outputting function 34e may limit the hierarchical layers of events to be displayed. The outputting function 34e is thereby able to control the amount of information to be provided to a user. FIG. 7 is a diagram illustrating an example of display according to the first embodiment.

Hierarchical display of events will be described below. Firstly, the managing function 34d manages events acquired by the event acquiring function 34c by hierarchizing the events, as illustrated in FIG. 8, for example. In the case illustrated in FIG. 8, four large events, "Start of procedure", "Contrast imaging of affected part", "Stent procedure", and "End of procedure", are included. FIG. 8 is a diagram for explanation of hierarchical display of events according to the first embodiment.

An image I21, an image I22, an image I23, and an image I24 have been associated with the event, "Start of procedure". Furthermore, "Start of procedure" includes, as a more detailed event, "Insertion of guide wire". The image I22 and the image I24 of the images associated with the event, "Start of procedure", have been associated with the event, "Insertion of guide wire". Furthermore, "Insertion of guide wire" includes, as a more detailed event, "Bifurcation check". The image I22 of the images associated with the event, "Insertion of guide wire", has been associated with the event, "Bifurcation check". As described above, more images are associated with an event in an upper hierarchical layer (a larger event) and the number of images associated is narrowed down for an event in a lower hierarchical layer (a more detailed event). Similarly, "Contrast imaging of affected part" includes, as a more detailed event, "Contrast imaging of affected part". Furthermore, "Stent procedure" includes "Stent placement" as a more detailed event.

In addition, "Stent placement" includes, as more detailed events, "Stent positioning", "Dilation", and "Check after dilation".

Figure 9A:
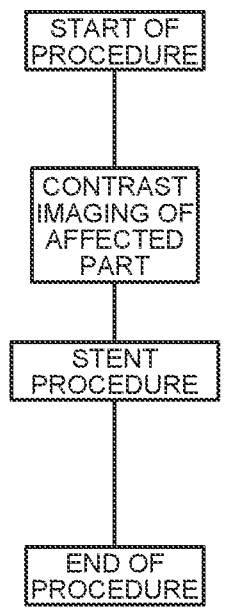
FIG. 9A is a diagram illustrating an example of display according to the first embodiment.
Figure 9B:
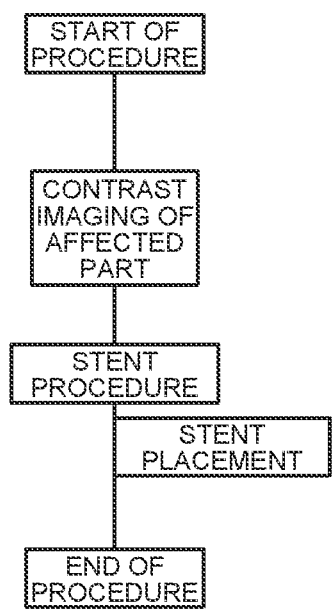
FIG. 9B is a diagram illustrating an example of display according to the first embodiment.

The outputting function 34e controls display on the basis of the events hierarchically managed as illustrated in FIG. 8. For example, as illustrated in FIG. 9A and FIG. 9B, the outputting function 34e displays events of hierarchical layers according to an input operation received from a user. FIG. 9A and FIG. 9B are diagrams illustrating examples of display according to the first embodiment.

Specifically, the outputting function 34e firstly displays four large events, "Start of procedure", "Contrast imaging of affected part", "Stent procedure", and "End of procedure", as illustrated in FIG. 9A. In a case where a user performs an operation for selecting "Stent procedure", for example, the outputting function 34e additionally displays "Stent placement" that is a detailed event included in the "Stent procedure". The outputting function 34e is thereby able to provide a detailed event according to a user's request while avoiding providing excess information to the user.

Figure 10A:
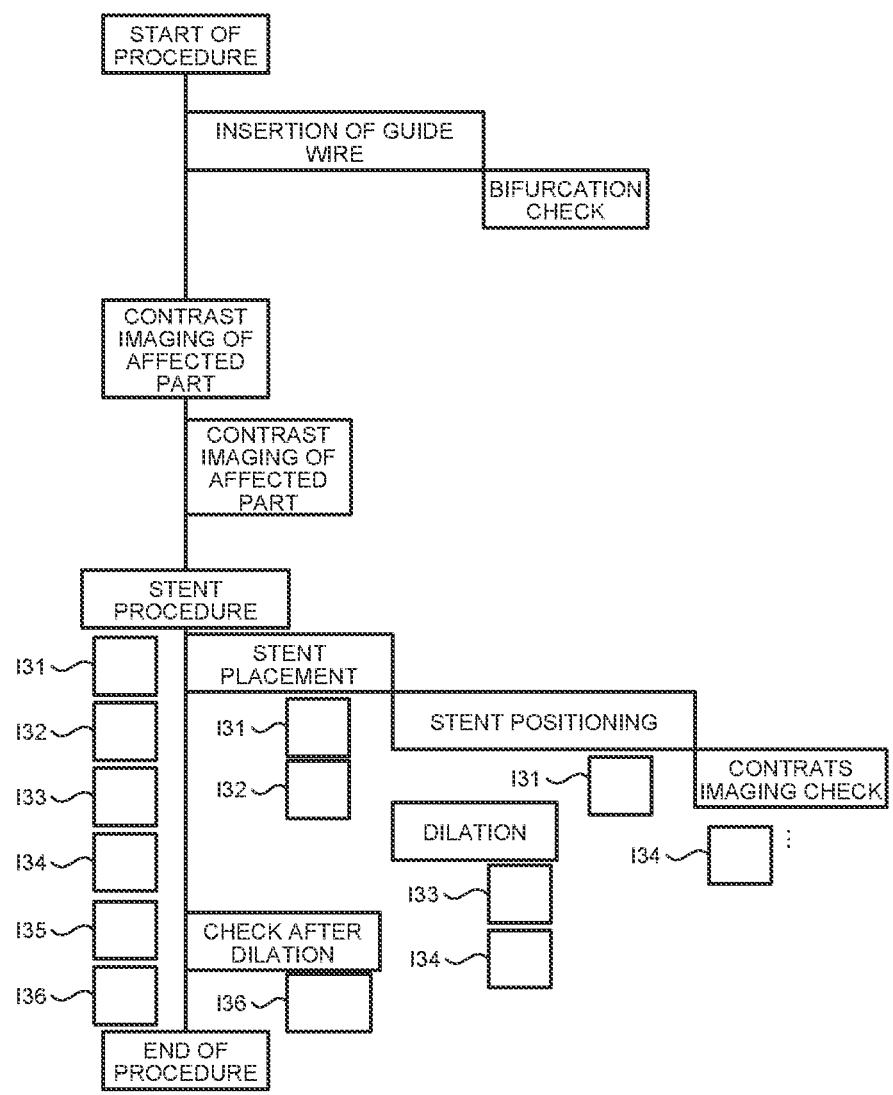
FIG. 10A is a diagram illustrating an example of display according to the first embodiment.
Figure 10B:
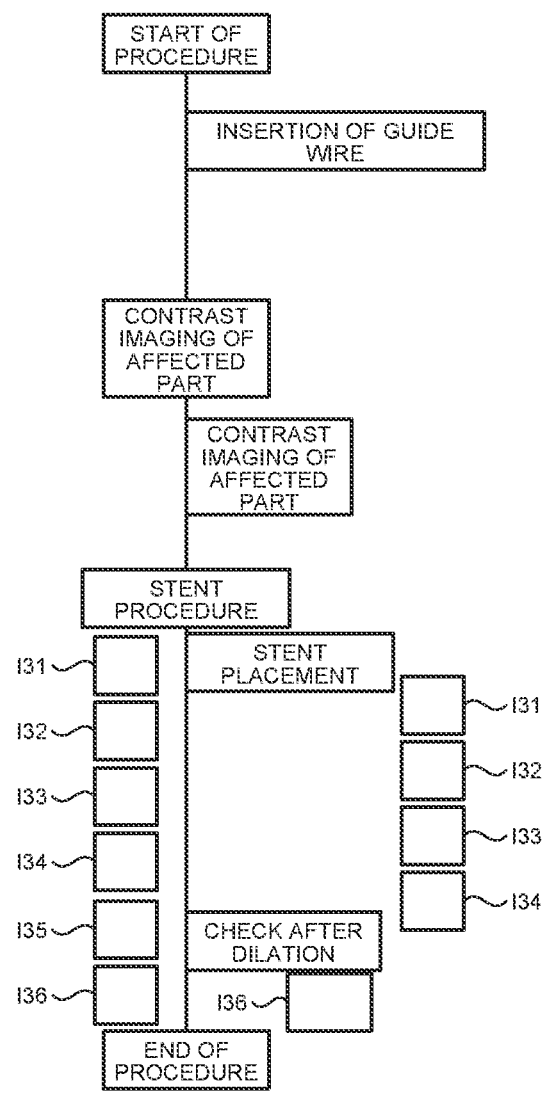
FIG. 10B is a diagram illustrating an example of display according to the first embodiment.

In another example, the outputting function 34e causes events of predetermined hierarchical layers to be displayed, as illustrated in FIG. 10A and FIG. 10B. FIG. 10A and FIG. 10B are diagrams illustrating examples of display according to the first embodiment.

For example, in a case where "four layers" have been set as predetermined hierarchical layers, the outputting function 34e displays, as illustrated in FIG. 10A, each of: events, such as "Start of procedure", "Contrast imaging of affected part", "Stent procedure", and "End of procedure", that are included in a first layer; events, such as "Insertion of guide wire", "Contrast imaging of affected part", "Stent placement", and "Check after dilation", that are included in a second layer; events, such as "Bifurcation check", "Stent positioning", and "Dilation", that are included in a third layer; and an event, such as "Contrast imaging check" that is included in a fourth layer. In a case where "two layers" have been set as predetermined hierarchical layers, the outputting function 34e displays, as illustrated in FIG. 10B, each of: events, such as "Start of procedure", "Contrast imaging of affected part", "Stent procedure", and "End of procedure", that are included in a first layer; and events, such as "Insertion of guide wire", "Contrast imaging of affected part", "Stent placement", and "Check after dilation", that are included in a second layer. That is, if "two layers" have been set as the predetermined hierarchical layers, the outputting function 34e may omit displaying hierarchical layers from a third layer. The outputting function 34e is thereby able to prevent confusion due to events being too detailed. The number of the predetermined hierarchical layers may be a preset value, a value automatically set by the outputting function 34e according to the total number of events, or any value set by a user.

As described above, according to the first embodiment, the image acquiring function 34b sequentially acquires medical images during a treatment procedure for the subject P. Furthermore, on the basis of the medical images, the event acquiring function 34c sequentially acquires events in the treatment procedure, during the treatment procedure. In addition, the managing function 34d manages the medical images and events, in association with temporal information on the treatment procedure. Furthermore, the outputting function 34e outputs a medical image such that a relation between the medical image and an event is able to be known. Therefore, the medical information processing apparatus 30 according to the first embodiment enables more effective utilization of medical images. For example, members of a team are able to know the current situation and communicate with one another readily, during a treatment procedure. Furthermore, for example, if use of a medical image that has been acquired in a treatment procedure is attempted during execution of the treatment procedure, the image needed is able to be retrieved readily.

In addition, as described above, according to the first embodiment, the outputting function 34e may also display a related image. An image needed is thereby able to be retrieved readily when use of the medical image is attempted during execution of a treatment procedure, for example.

Furthermore, as described above, according to the first embodiment, the managing function 34d manages events by hierarchizing the events. In addition, the outputting function 34e displays events of a hierarchical layer according to an input operation received from a user, or displays events of a predetermined hierarchical layer. The medical information processing apparatus 30 is thereby able to prevent a user from getting confused by having too much information being displayed.

Medical images have been described as being displayed on the display 32 such that relations between the medical images and events are able to be known but the embodiment is not limited to this example. For example, the outputting function 34e may generate the display screen illustrated in FIG. 5 or FIG. 7 and transmit the display screen to the X-ray diagnostic apparatus 10. In this case, the display illustrated in FIG. 5 or FIG. 7 may be performed on the display 108 that the X-ray diagnostic apparatus 10 has.

Second Embodiment

Figure 11:
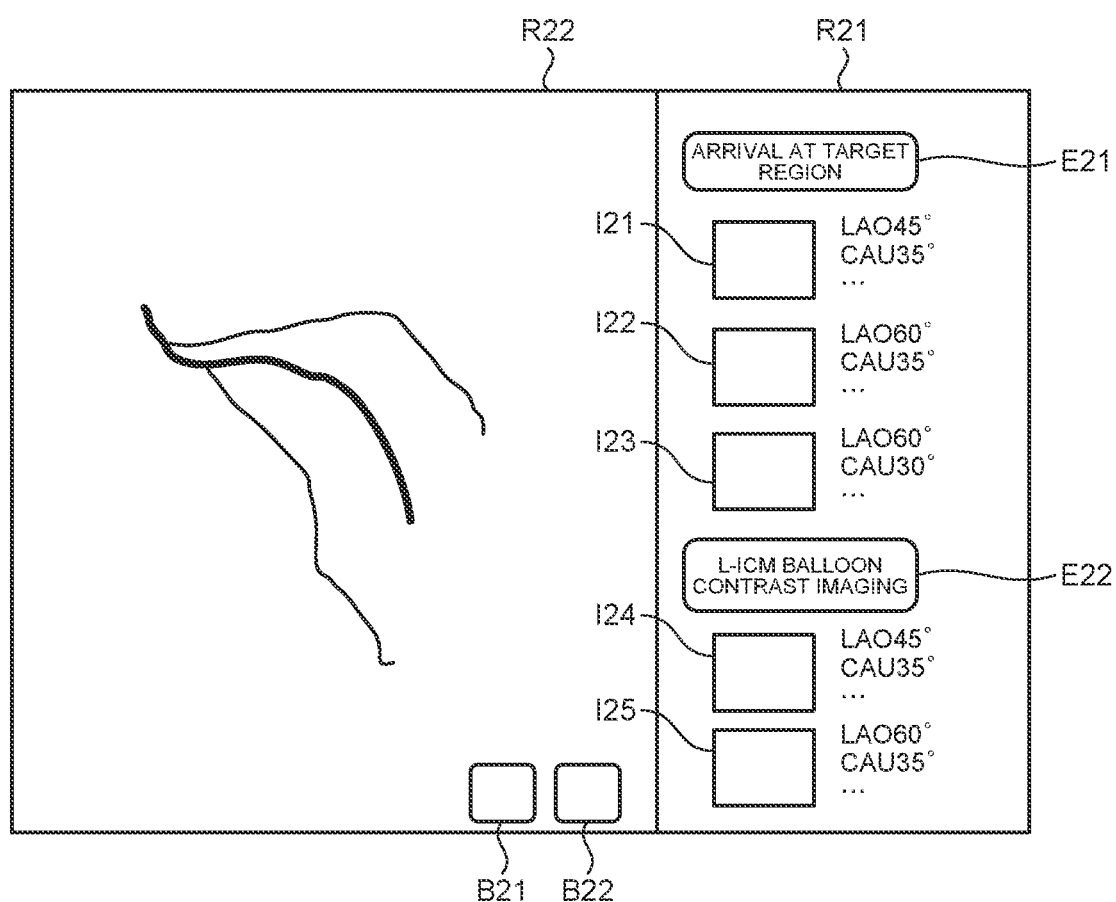
FIG. 11 is a diagram illustrating an example of display according to a second embodiment.

With respect to the first embodiment, the display screens in FIG. 5 and FIG. 7 have been described as display examples. In contrast, for a second embodiment, a display screen in FIG. 11 will be described as a display example. FIG. 11 is a diagram illustrating an example of display according to the second embodiment. A medical information processing system 1 according to the second embodiment has the same configuration as the medical information processing system 1 illustrated in FIG. 1 and FIG. 2 and a part of processing by an outputting function 34e thereof is different therefrom. Reference signs that are same as those in FIG. 1 and FIG. 2 will be assigned to components that are the same as those described already with respect to the first embodiment and description thereof will be omitted.

For example, as illustrated in FIG. 11, the outputting function 34e displays a display screen including an area R21 and an area R22 on a display 32. Specifically, the outputting function 34e displays a timeline having events arranged chronologically in the area R21 and displays medical images acquired during a treatment procedure on the timeline. That is, the outputting function 34e displays a timeline having events arranged chronologically and displays medical images such that chronological relations between the medical images and the events displayed in the timeline are able to be known.

Specifically, in the case illustrated in FIG. 11, the treatment procedure includes an event E21, "Arrival at target region" and an event E22, "L-ICM balloon contrast imaging". Furthermore, in the event E21, an X-ray image I21, an X-ray image I22, and an X-ray image I23 are sequentially acquired, and in the event E22, an X-ray image I24 and an X-ray image I25 are sequentially acquired. Similarly to the cases in FIG. 5 and FIG. 7, the outputting function 34e may also display a related image, such as an ultrasound image, in addition to the X-ray images acquired during the treatment procedure. Furthermore, the outputting function 34e may display an icon B21 and an icon B22, for example, and narrow down related images to be displayed, according to an operation on these icons.

Furthermore, as illustrated in FIG. 11, the outputting function 34e may display arm position information on the acquisition of the X-ray images. Specifically, the outputting function 34e may display that the X-ray image I21 was acquired at "LAO 45° and CAU 35°", the X-ray image I22 was acquired at "LAO 60° and CAU 35°", the X-ray image I23 was acquired at "LAO 60° and CAU 30°", the X-ray image I24 was acquired at "LAO 45° and CAU 35°", and the X-ray image I25 was acquired at "LAO 60° and CAU 35°".

Image reproduction is thereby able to be performed efficiently, for example. In a case where a user refers to the display screen in FIG. 11 during a treatment procedure and determines that an image having an imaging angle similar to that of the X-ray image I21 is preferably used in the current situation, for example, the user rotates a C-arm 105 to "LAO 45° and CAU 35°". A user is thereby able to proceed with the treatment procedure more efficiently using a real-time image of a desired angle.

The outputting function 34e may display arm position information that has been used for the longest period of time during a treatment procedure by highlighting the arm position information in the area R21 of FIG. 11. That is, the outputting function 34e may estimate and display the main working angle. Such a working angle is often an angle at which useful images are able to be acquired during that treatment procedure and image reproduction at that working angle is needed comparatively often. Therefore, displaying the arm position information used for the longest time period during the treatment procedure by highlighting the arm position information enables more efficient image reproduction.

Third Embodiment

Figure 12:
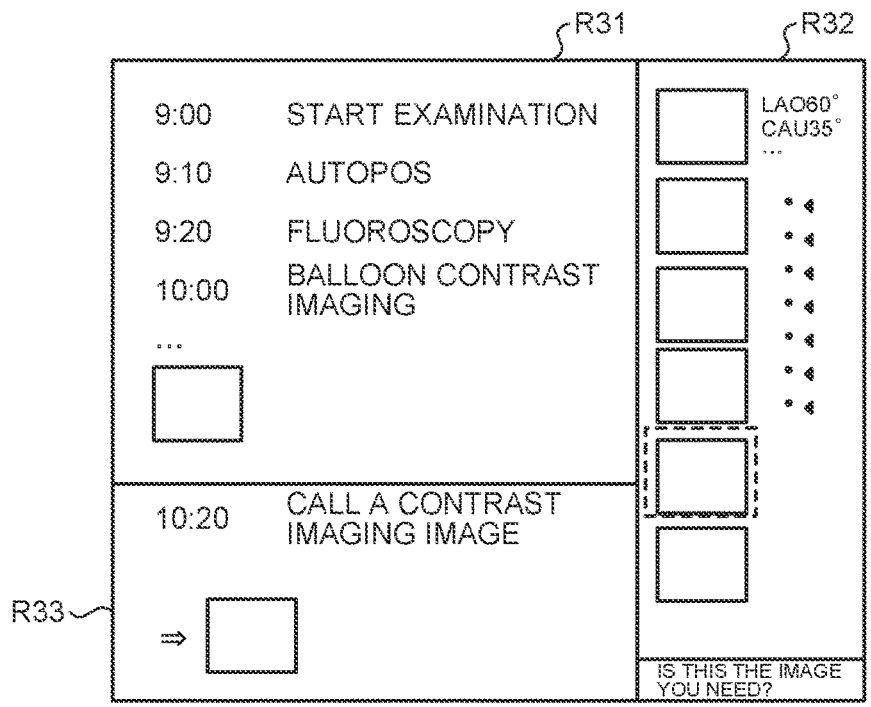
FIG. 12 is a diagram illustrating an example of display according to a third embodiment.

With respect to the first and second embodiments, the display screens in FIG. 5, FIG. 7, and FIG. 11 have been described above as display examples. In contrast, for a third embodiment, a display screen in FIG. 12 will be described as a display example. FIG. 12 is a diagram illustrating an example of display according to the third embodiment. A medical information processing system 1 according to the third embodiment has the same configuration as the medical information processing system 1 illustrated in FIG. 1 and FIG. 2 and a part of processing by an outputting function 34e thereof is different therefrom. Reference signs that are the same as those in FIG. 1 and FIG. 2 will be assigned to components that are the same as those described already with respect to the first and second embodiments and description thereof will be omitted.

For example, as illustrated in FIG. 12, the outputting function 34e displays a display screen including an area R31, an area R32, and an area R33 on a display 32. Specifically, the outputting function 34e displays a timeline having events arranged chronologically in the area R31. Furthermore, the outputting function 34e displays medical images acquired during a treatment procedure, in the area R32. In a case of displaying X-ray images as the medical images, the outputting function 34e may display arm position information on acquisition of the X-ray images, as illustrated in FIG. 12.

Furthermore, the outputting function 34e displays information on input and output performed between the outputting function 34e and a user, in the area R33. For example, a user inputs, through voice input or a keyboard operation, "Call a contrast imaging image." In response to this input, the outputting function 34e retrieves an X-ray image resulting from contrast imaging of a blood vessel of the subject P from the X-ray images acquired during the treatment procedure, and displays the retrieved X-ray image in the area R33. As described above, the outputting function 34e displays a medical image according to an input operation received from a user and displays information in the area R33, the information being on input and output performed between the outputting function 34e and the user until the medical image was displayed.

That is, the outputting function 34e is artificial intelligence (AI) that receives an input operation from a user and displays a medical image and the outputting function 34e may display exchanges performed between the outputting function 34e and the user, in the area R33. The user is thereby able to readily check any image needed. For example, a command input to call a medical image is displayed with the medical image in the area R33 and with what intent that medical image has been called is thus able to be known at a glance.

Fourth Embodiment

Figure 13:
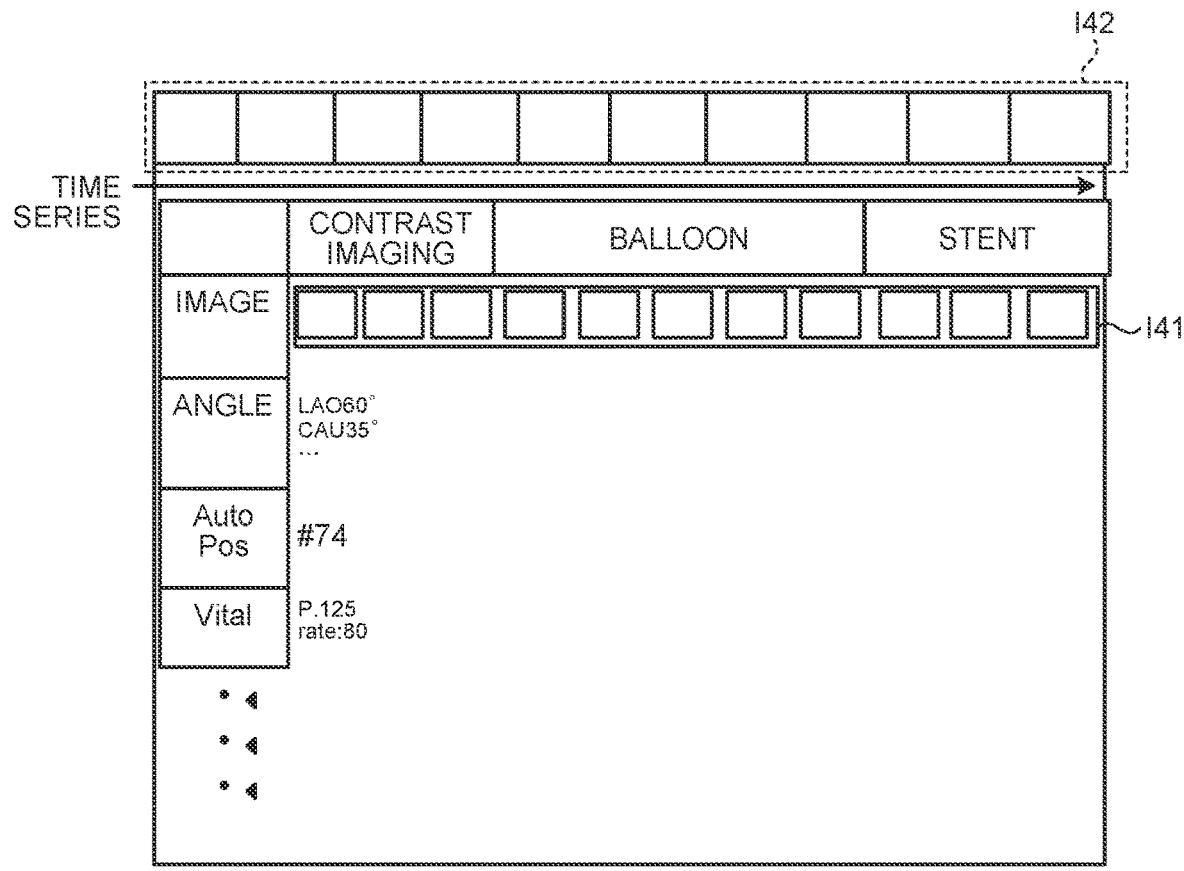
FIG. 13 is a diagram illustrating an example of display according to a fourth embodiment.

With respect to the first to third embodiments, the display screens in FIG. 5, FIG. 7, FIG. 11, and FIG. 12 have been described above as display examples. In contrast, for a fourth embodiment, a display screen in FIG. 13 will be described as a display example. FIG. 13 is a diagram illustrating an example of display according to the fourth embodiment. A medical information processing system 1 according to the fourth embodiment has the same configuration as the medical information processing system 1 illustrated in FIG. 1 and FIG. 2 and a part of processing by an outputting function 34e thereof is different therefrom. Reference signs that are the same as those in FIG. 1 and FIG. 2 will be assigned to components that are the same as those described already with respect to the first and second embodiments and description thereof will be omitted.

For example, as illustrated in FIG. 13, the outputting function 34e displays a timeline having events, such as "Contrast imaging", "Balloon", and "Stent", arranged chronologically, and also displays plural medical images I41 such that chronological relations between the plural medical images I41 and these events are able to be known. Furthermore, the outputting function 34e also displays supplementary information for the medical images. For example, the outputting function 34e displays supplementary information, such as "Angle", "AutoPos", and "Vital", for each of the medical images. These pieces of supplementary information may be stored in a DICOM tag of each medical image, for example. For example, by referring to these pieces of supplementary information, a user is able to more readily find any image that the user desires to check.

Furthermore, the outputting function 34e may also display an examination room interior image. For example, as illustrated in FIG. 13, the outputting function 34e may display plural examination room interior images I42. Specifically, during the treatment procedure, the image acquiring function 34b sequentially acquires examination room interior images having captured therein the interior of the examination room during the treatment procedure. These examination room interior images are, for example, plural frames included in a moving image captured using an optical camera. In addition, a managing function 34d manages, in addition to the medical images and the events, the examination room interior images, in association with temporal information.

Furthermore, as illustrated in FIG. 13, the outputting function 34e displays the timeline having the events, such as "Contrast imaging, "Balloon", and "Stent", chronologically arranged. In addition, the outputting function 34e displays the plural medical images I41 such that the chronological relations between the plural medical images I41 and the events displayed in the timeline are able to be known. The outputting function 34e also displays the examination room interior images I42 in association with the timeline. That is, the outputting function 34e displays the events, "Contrast imaging", "Balloon", and "Stent", the plural medical images I41, and the plural examination room interior images I42 such that their horizontal axes (time series) match one another. For example, by referring to the examination room interior images during execution of the procedure, the user is able to get an overview of the procedure and the medical images are able to be utilized for improvement of the efficiency of the procedure.

Fifth Embodiment

The first to fourth embodiments have been described thus far, but various different embodiments other than the embodiments described above are possible.

For example, with respect to the examples illustrated in FIG. 5, FIG. 7, FIG. 11, FIG. 12, and FIG. 13, the case where at least a timeline having events arranged chronologically is displayed has been described. However, the embodiments are not limited to this case. For example, the outputting function 34e may omit the display of a timeline, and may display medical images associated with an event received from a user through voice or a keyboard, for example.

Furthermore, for example, with respect to the embodiments described above, the case where the processing circuitry 34 of the medical information processing apparatus 30 executes functions, such as the event acquiring function 34c, the managing function 34d, and the outputting function 34e has been described. However, the embodiments are not limited to this case, and for example, the processing circuitry 110 of the X-ray diagnostic apparatus 10 may execute functions corresponding to the event acquiring function 34c, the managing function 34d, and the outputting function 34e.

For example, the processing circuitry 110 further executes an event acquiring function 110d and a managing function 110e not illustrated in the drawings. For example, the acquiring function 110b sequentially acquires X-ray images on the basis of X-rays transmitted through the subject P during a treatment, procedure for the subject P. Furthermore, on the basis of the X-ray images, the event acquiring function 110d sequentially acquires events in the treatment procedure, during the treatment procedure. Furthermore, the managing function 110e manages the X-ray images and the events, in association with temporal information on the treatment procedure. The outputting function 110c then outputs the X-ray images such that relations between the X-ray images and the events are able to be known. For example, the outputting function 110c may display the display screen in FIG. 5, FIG. 7, FIG. 11, FIG. 12, or FIG. 13, on the display 108.

The acquiring function 110b may acquire X-ray images again on the basis of a acquisition condition for an X-ray image that has been selected by a user from the X-ray images output by the outputting function 110c. For example, in a case where the outputting function 110c displays the display screen in FIG. 11 on the display 108 and a user selects the X-ray image I21, the acquiring function 110b acquires X-ray images again for the condition, "LAO 45° and CAU 35°". In a case where a predetermined operation button is pressed while the X-ray image I21 is being displayed in the area R22, for example, the acquiring function 110b determines that the X-ray image I21 has been selected and executes acquisition of X-ray images for the condition, "LAO 45° and CAU 35°". Image reproduction is thereby able to be performed more efficiently.

The term, "processor", used in the description above means, for example, a circuit, such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). In a case where the processor is a CPU, for example, the processor implements the functions by reading and executing programs stored in a storage circuit. In a case where the processor is, for example, an ASIC, instead of the programs being stored in a storage circuit, the functions are directly incorporated, as logic circuits, in the circuit of the processor. Each of the processors according to the embodiments is not necessarily configured as a single circuit, and plural independent circuits may be combined together to be configured as a single processor to implement their functions. Plural components in each drawing may also be integrated into a single processor to implement their functions.

The components of each apparatus according to the embodiments described above have been functionally and conceptually illustrated in the drawings and are not necessarily configured physically as illustrated in the drawings. That is, specific forms of distribution and integration of the apparatuses are not limited to those illustrated in the drawings, and all or a part of each apparatus may be configured to be distributed or integrated functionally or physically in any units, according to various loads and/or use situations, for example. In addition, all or any part of the processing functions executed in the apparatuses may be implemented by a CPU and a program analyzed and executed by the CPU or implemented as hardware by wired logic.

Furthermore, any medical information processing method described above with respect to the embodiments may be implemented by a computer, such as a personal computer or a work station, executing a medical information processing program that has been prepared beforehand. This medical information processing program may be distributed via a network, such as the Internet. Furthermore, this medical information processing program may be recorded in a computer-readable non-transitory recording medium, such as a hard disk, a flexible disk (FD), a CD-ROM, an MO, or a DVD, and executed by being read by a computer from the recording medium.

According to at least one of the embodiments described above, medical images are able to be utilized more effectively.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
   processing circuitry configured to:
      sequentially acquire medical images during a treatment procedure for a subject;
      sequentially identify images in which events that indicate a phase of the treatment procedure have occurred, from the medical images sequentially acquired, based on the medical images sequentially acquired; and
      store the medical images acquired and also store information on the events that have occurred, in association with the identified images in which the events have occurred, the identified images being from the medical images stored.

2. The medical information processing apparatus according to claim 1, wherein the processing circuitry is further configured to cause a display to display the stored medical images, such that chronological relationships between the stored medical images and the events that have occurred are able to be recognized.

3. The medical information processing apparatus according to claim 2, wherein the processing circuitry is further configured to cause the display to display a timeline having the events arranged chronologically based on temporal information and also display the medical images such that the chronological relationships between the stored medical images and the events displayed in the timeline are able to be known.

4. The medical information processing apparatus according to claim 3, wherein the processing circuitry is further configured to cause a related image related to the medical images to be displayed.

5. The medical information processing apparatus according to claim 4, wherein the processing circuitry is further configured to cause the related image related to the medical images to be displayed, wherein the related image is an image having supplementary information that is identical to or similar to that of the medical images or an image having image features similar to those of the medical images.

6. The medical information processing apparatus according to claim 4, wherein the processing circuitry is further configured to cause the related image related to the medical images to be displayed, wherein the related image is an image acquired using an apparatus different from an apparatus for the medical images.

7. The medical information processing apparatus according to claim 4, wherein the processing circuitry is further configured to cause the related image related to the medical images to be displayed, wherein the related image is a processed image that has been generated based on the medical images.

8. The medical information processing apparatus according to claim 4, wherein the medical images are X-ray images acquired using an X-ray diagnostic apparatus, and the processing circuitry is further configured to cause the X-ray images to be displayed such that relationships between the X-ray images and the events are able to be known, and also cause an X-ray image to be displayed, the X-ray image having arm position information that is the same as or similar to that of the X-ray images.

9. The medical information processing apparatus according to claim 4, wherein the medical images are X-ray images acquired using an X-ray diagnostic apparatus, and the processing circuitry is further configured to cause the X-ray images to be displayed such that relationships between the X-ray images and the events are able to be known, and also cause the related image to be displayed, the related image being a two-dimensional medical image that has been generated from a three-dimensional medical image based on arm position information of the X-ray images.

10. The medical information processing apparatus according to claim 4, wherein the processing circuitry is further configured to cause the related image to be displayed by processing or generating the related image according to the medical images.

11. The medical information processing apparatus according to claim 3, wherein the medical images are X-ray images acquired using an X-ray diagnostic apparatus, and the processing circuitry is further configured to cause the X-ray images to be displayed such that relationships between the X-ray images and the events are able to be known and also cause arm position information to be displayed, the arm position information being information on an arm position at the time of acquisition of the X-ray images.

12. The medical information processing apparatus according to claim 3, wherein the processing circuitry is further configured to cause the medical images to be displayed according to an input operation received from a user and also cause information to be displayed, the information being on input and output performed between the processing circuitry and the user until the medical images were displayed.

13. The medical information processing apparatus according to claim 3, wherein the processing circuitry is further configured to:

sequentially acquire, during the treatment procedure, examination room interior images having, captured therein, the interior of an examination room during the treatment procedure;

manage the medical images, the events, and the examination room interior images, in association with the temporal information; and cause a timeline to be displayed based on the temporal information, the timeline having the events arranged chronologically, cause the medical images to be displayed such that chronological relationships between the medical images and the events displayed in the timeline are able to be known, and cause the examination room interior images to be displayed in association with the timeline.

14. The medical information processing apparatus according to claim 13, wherein the processing circuitry is further configured to cause the medical images to be displayed with supplementary information of the medical images.

15. The medical information processing apparatus according to claim 3, wherein the processing circuitry is further configured to:

manage the events by hierarchizing the events; and cause the events to be displayed, the events being of a hierarchical layer corresponding to an input operation received from a user.

16. The medical information processing apparatus according to claim 3, wherein the processing circuitry is further configured to manage the events by hierarchizing the events, and the display displays the events of a predetermined hierarchical layer.

17. The medical information processing apparatus according to claim 1, wherein the processing circuitry is further configured to acquire an event in the treatment procedure based on a database storing event types.

18. An X-ray diagnostic apparatus, comprising:

processing circuitry configured to:

sequentially acquire X-ray images based on X-rays transmitted through a subject during a treatment procedure for the subject;

sequentially acquire events that indicate a phase of the treatment procedure based on the X-ray images acquired during the treatment procedure;

store the X-ray images and the events, in association with temporal information on the treatment procedure; and output the X-ray images such that relations between the X-ray images and the events are able to be known.

19. The X-ray diagnostic apparatus according to claim 18, wherein the processing circuitry is further configured to execute acquisition of X-ray images again based on an acquisition condition for an X-ray image selected by a user from the output X-ray images.

20. A non-transitory computer-readable medium storing a medical information processing program that, when executed, causes a computer to execute a method comprising:

sequentially acquiring medical images during a treatment procedure for a subject;

sequentially acquiring events that indicate a phase of the treatment procedure based on the medical images acquired during the treatment procedure;

storing the medical images and the events, in association with temporal information on the treatment procedure; and outputting the medical images such that relations between the medical images and the events are able to be known.

* * * * *